United States Patent [19]

Hampden-Smith et al.

[11] Patent Number: 5,744,198
[45] Date of Patent: Apr. 28, 1998

[54] METHOD OF DEPOSITING METAL SULFIDE FILMS FROM METAL THIOCARBOXYLATE COMPLEXES WITH MULTIDENTATE LIGANDS

[75] Inventors: Mark Hampden-Smith; Klaus Kunze; May Nyman, all of Albuquerque, N. Mex.

[73] Assignee: The University of New Mexico, Albuquerque, N. Mex.

[21] Appl. No.: 607,363

[22] Filed: Feb. 27, 1996

[51] Int. Cl.$^6$ .................. B05C 3/02; B05C 5/06
[52] U.S. Cl. .................. 427/376.6; 427/163.3; 427/226
[58] Field of Search .................. 427/74, 75, 431, 427/432, 435, 376.6, 226, 163.3

[56] References Cited

U.S. PATENT DOCUMENTS

| | | | |
|---|---|---|---|
| 4,360,542 | 11/1982 | Loeffler et al. | 427/75 |
| 4,681,777 | 7/1987 | Engelken et al. | 427/255.2 |
| 4,812,333 | 3/1989 | Micheli | |
| 4,885,188 | 12/1989 | Hasegawa et al. | |
| 5,110,622 | 5/1992 | Hasegawa et al. | 427/64 |
| 5,112,410 | 5/1992 | Chen | 427/74 |
| 5,273,774 | 12/1993 | Karam et al. | 427/255.2 |
| 5,304,281 | 4/1994 | Wang | 427/586 |

FOREIGN PATENT DOCUMENTS 62146272  6/1987  Japan.

*Primary Examiner*—Shrive P. Beck
*Assistant Examiner*—Bret Chen
*Attorney, Agent, or Firm*—Robert W. Becker & Associates; Gudrun E. Huckett

[57] ABSTRACT

In a method of depositing a metal sulfide film on a substrate, at least one metal compound precursor comprising at least one thiocarboxylate ligand SECR and at least one solubility-improving ligand L is dissolved in a solvent to produce a solution, wherein a) E is selected from the group consisting of O and S and R is selected from the group consisting of alkyl, aryl, substituted alkyl, substituted aryl, halogenated alkyl, and halogenated aryl; and wherein b) L is selected from the group of monodentate ligands, multidentate ligands, and $R^1O$ ligands. The solution is coated onto a substrate and the substrate is heated to a reaction temperature sufficient to decompose the metal compound precursor to form a metal sulfide film of at least one metal on the substrate.

19 Claims, 15 Drawing Sheets

METHOD OF DEPOSITING METAL SULFIDE FILMS FROM METAL THIOCARBOXYLATE COMPLEXES WITH MULTIDENTATE LIGANDS

The US Government may have specific rights regarding this invention as provided for in the terms of Contract N00014-91-J1258 awarded by the Office of Naval Research.

FIELD OF THE INVENTION

The present invention is in the field of deposition of metal sulfides on substrates for application in display technology.

BACKGROUND OF THE INVENTION

Thin film deposition describes a group of techniques for forming a layer of a solid material on a substrate. The layer or film should be homogenous, uniform in thickness, pure and generally crystalline to achieve the most desirable properties. The films deposited for application in display technology are generally required to have all these properties because they are critical to the success of the whole display. Film deposition techniques include vapor phase processes such as physical vapor deposition or chemical vapor deposition (CVD), liquid phase processes such as spin-coating or dip coating and solid state deposition processes which generally involve sintering a powder at high temperatures. The solid-state route is generally unacceptable for the formation of films to be integrated into electronic devices as a result of the high temperatures required to form the desired properties outlined above.

Metal sulfide thin films, particularly those of the group 2 elements, including CaS, SrS, and BaS, the group 12 elements, including ZnS and CdS, and the group 13 elements, including GaS, $Ga_2S_3$, InS, and $In_2S_3$, and combinations thereof, are of interest in applications for display technologies because they can act as host crystalline lattices for rare-earth dopants that exhibit luminescent properties. However, the deposition of metal sulfide films, especially group 2 metal sulfide films, is difficult because suitable soluble sources of these elements are not readily available. Furthermore, it is desirable to use one compound as a source of the group 2, 12, or 13 element and S (often defined as a "single-source precursor" since the metal and sulfur are already present in the desired stoichiometric ratio in a single compound) to aid control over the stoichiometry (M:S ratio) in the final film. At present, few single-source precursors that are soluble in organic solvents are available for the formation of especially group 2 metal sulfide films. For commercial exploitation more work is required to develop better preparative methods for the formation of especially group 2 metal sulfide films. This patent application is concerned with the synthesis and characterization of a general class of single-source precursors of especially group 2, 12, and 13 metals and other metals and their conversion to metal sulfide films via liquid phase techniques.

Very little prior art exists in the use of single-source precursors for the formation of group 2 metal sulfide films by liquid phase routes. The formation of strontium sulfide has been achieved from the thermal decomposition of organic solution of strontium laurylmercaptide at 450° C. for 1 hr (Isozaki, et al., JP 62146272 A2 870630 Showa; JP 85-286069 851219). However, this process cannot be generalized for the formation of other group 2 metal sulfide films or other metal sulfide films from organic solutions of group 2 metal-containing or other metal-containing precursors.

U.S. Pat. No. 4,812,333 discloses the use of organometallic compounds with a metal-sulfur bond, for example, thiocarboxylates, in combination with dissolved sulfur to be applied to a substrate and heated for decomposition to a metal sulfide film. The precursor is dissolved in the presence of sulfur as a solubilizing aid in pyridine or $CS_2$. Metals mentioned are Zn, Cd, Cu, Pb.

U.S. Pat. No. 5,110,622 uses organometallic compounds, for example, thiocarboxylates, dissolved in aromatic solvents for spray-coating on a substrate and subsequent heating in argon to form a metal sulfide film.

U.S. Pat. No. 4,885,188 uses a hydrocarbon solution of organometallic compounds, for example, thiocarboxylates, for spin-coating etc. on a substrate and subsequent heating in nitrogen in the presence of $H_2S$ to decompose the precursor and form a metal sulfide film.

These three references disclose the use of thiocarboxylates as a precursor for the formation of metal sulfide films by thermal decomposition. The use of cyclic or acyclic ethers or amines such as crown ethers or like compounds which can act as monodentate or multidentate ligands as a solubility enhancer and to make these compounds available for liquid phase techniques is not disclosed.

It is an object of the present invention to provide a method for the deposition of metal sulfide films from single-source precursors by liquid phase metal-organic decomposition.

SUMMARY OF THE INVENTION

The method of depositing a metal sulfide film on a substrate is primarily characterized by the following steps:

dissolving in a solvent at least one metal compound precursor, said metal compound precursor comprising at least one thiocarboxylate ligand SECR and at least one solubility-improving ligand L, to produce a solution, wherein:

a) E is selected from the group consisting of O and S and R is selected from the group consisting of alkyl, aryl, substituted alkyl, substituted aryl, halogenated alkyl, and halogenated aryl; and b) L is selected from the group of monodentate ligands, multidentate ligands, and $R^1O$ ligands; coating the solution onto a substrate; and heating the substrate to a reaction temperature sufficient to decompose the metal compound precursor to form a metal sulfide film of at least one metal on the substrate.

The metal of the metal compound precursor is preferably selected from the group consisting of Ca, Sr, Ba, Zn, Cd, Pb, Ga, In, Sb, and Bi.

The metal compound precursor is preferably $M(SECR)_n L_m$.

The metal compound precursor may be $(R^1O)_n M(SECR)_m$ with $R^1$ selected from the group consisting of alkyl, aryl, substituted alkyl, and substituted aryl.

The method may further comprise the step of providing during heating an inert atmosphere for the substrate and the metal sulfide film.

The method further includes the step of selecting the reaction temperature to be between 100° C. and 1000° C. Preferably, the reaction temperature is between 400° C. and 700° C.

The method may further include the step of selecting the multidentate ligand from the group consisting of cyclic polyethers, acyclic polyethers, cyclic polyamines, and acyclic polyamines. The acyclic polyethers may include diglyme, triglyme, tetraglyme, and derivatives of diglyme, triglyme, and tetraglyme. The polyamines may include ethylene diamine and derivatives thereof and diethylene triamine and derivatives thereof.

Preferably, the method further includes the step of selecting the multidentate ligand from the group of crown ethers. The group of crown ethers may includes 18-crown-6 ether and derivatives thereof and 15-crown-5ether and derivatives thereof.

The monodentate ligand are preferably selected from the group consisting of an ether and an amine.

The method may further comprise the step of annealing at a preset annealing temperature the metal sulfide film formed on the substrate.

The method may further include the steps of adding to the solution at least one dopant compound comprising a metal dopant selected from the group consisting of Cu, Ag, Au, Eu, Dy, Ho, Er, Tb, Pr, and Ce and selecting a concentration of the metal dopant to be less than 10 weight-% of the metal sulfide film.

The solution may contain a first one of the metal compound precursors and a second one of the metal compound precursors to produce a mixed metal sulfide film, wherein the first metal compound precursor contains a different metal than the second metal compound precursor.

The solution may further contain a third one of the metal compound precursors and the third metal compound precursor contains a different metal than the first and the second metal compound precursors.

The method includes also the steps of adding to the solution of the first and the second metal compound precursors at least one dopant compound comprising a metal dopant selected from the group consisting of Mn, Cu, Ag, Au, Eu, Dy, Ho, Er, Tb, Pr, and Ce and selecting a concentration of the metal dopant to be less than 10 weight-% of the mixed metal sulfide film.

The method may also comprise the step of selecting the substrate from a group consisting of a silicon substrate, a glass substrate, an indium tin oxide substrate, and an aluminum tin oxide substrate.

The present invention provides a method for depositing metal sulfide films and doped metal sulfide films, especially group 2 metal sulfides, MS (M=Ca, Sr, Ba), group 12 metal sulfides, ZnS and CdS, and group 13 metal sulfides, GaS, $Ga_2S$, InS, and $In_2S_3$, and combinations thereof, e.g., to form $MM'_2S_4$ where M=Ca Sr, Ba, Zn, Cd, and M'=Ga, In, from single-source precursors of the general formula $M(SECR)_n \cdot L_m$ or $(R'O)_n \cdot M(SECR)_m$, where n and m are integers and depend on the valences of the metal, E=O or S, L=multidentate ligand such as 18-crown-6, 15-crown-5, tetraglyme or polyamine, and R=any alkyl, substituted alkyl, aryl, substituted aryl, halogenated alkyl and halogenated aryl, or any other metal compound containing at least one thiocarboxylate ligand and at least one further ligand to increase solubility.

It should be noted that the present invention is not limited to the aforementioned metals of groups 2, 12, 13, but is generally is suitable for all metals, in particular also transition elements and lanthanides.

Non-limiting examples for R=alkyl substituents, including substituted and halogenated substituents, are: methyl, ethyl, tert-butyl, neopentyl, $CF_3$. Non-limiting examples for R=aryls are: phenyl, toluyl, xylyl, cyclopentadiene.

The alkyloxides or aryloxides of the $R^1O_nM(SECR)_m$ precursors may include, as non-limiting examples, those with $R^1$=alkyl substituents, including substituted and halogenated substituents, such as i-propyl, tert-butyl, and neopentyl. Non-limiting examples for $R^1$=aryls are: phenyl, toluyl, xylyl, cyclopentadiene.

The alkyloxide or aryloxide substituents enhance the solubility and volatility of the metal thiocarboxylate precursors. Likewise, the monodentate or multidentate ligands L render the title compounds more soluble than in the absence of L. As a result, these compounds are suitable for the deposition of metal sulfide films by liquid phase metal-organic decomposition.

The metal sulfide films formed are stoichiometric and pure as a result of the elimination of the organic ligands, for example, according to the proposed reaction $M(SECR)_n \cdot L_m \rightarrow MS + n/2 (RCE)_2S + mL$. Depending on the valences of the metal, metal sulfides of other stoichiometry such as $M_2S_3$ will be formed). This invention shows how these compounds, especially where M=Ca, Sr, Ba, Zn, Cd, Ga, In, E=O, and R=methyl (i.e., thioacetate substituent MeCOS, abbreviated in the following as SAc), can be used to deposit crystalline metal sulfide films on any suitable substrate by liquid phase metal-organic decomposition.

BRIEF DESCRIPTION OF THE DRAWINGS

The object and advantages of the present invention will appear more clearly from the following specification in conjunction with the accompanying tables and drawings, in which.

DESCRIPTION OF PREFERRED EMBODIMENTS

Figure 1:
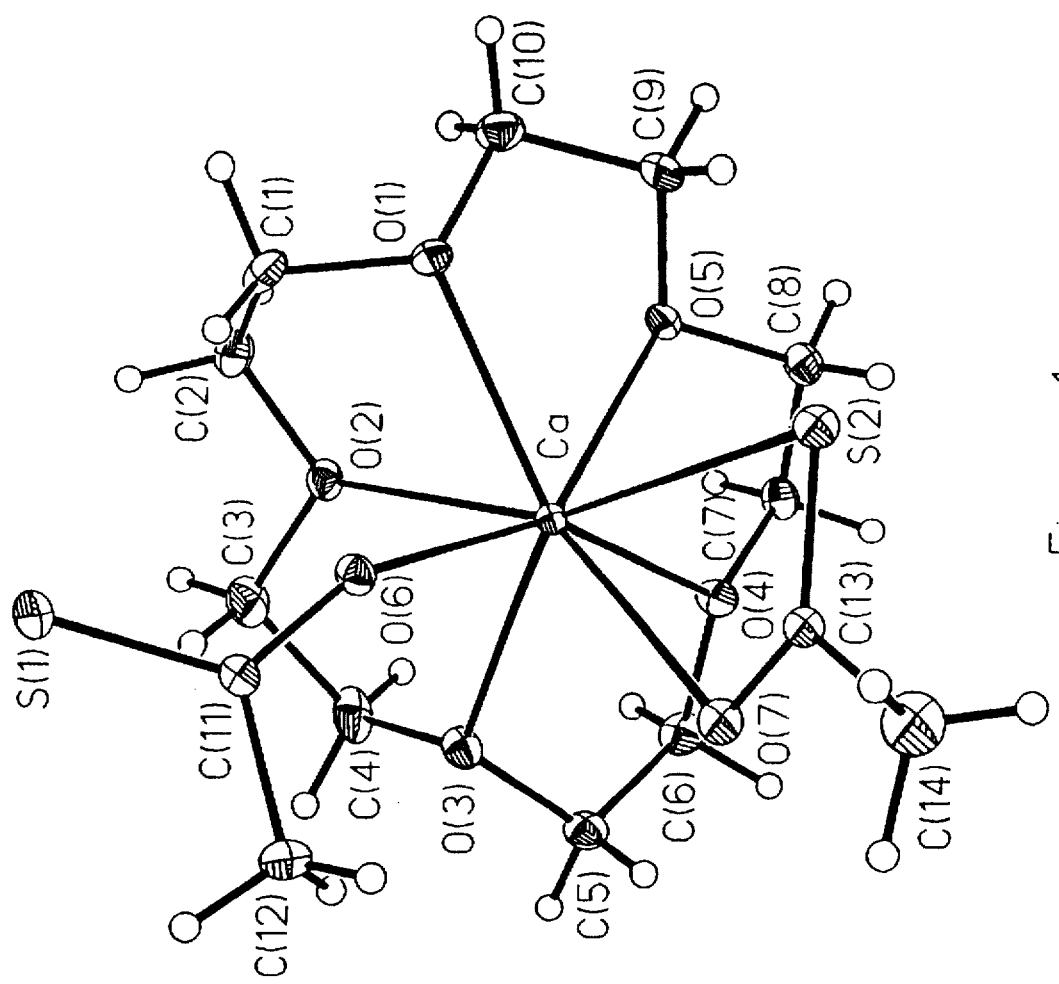
FIG. 1 shows the crystal structure of $Ca(SAc)_2 \cdot 15$crown-15-crown-5 in the solid state.
Figure 2:
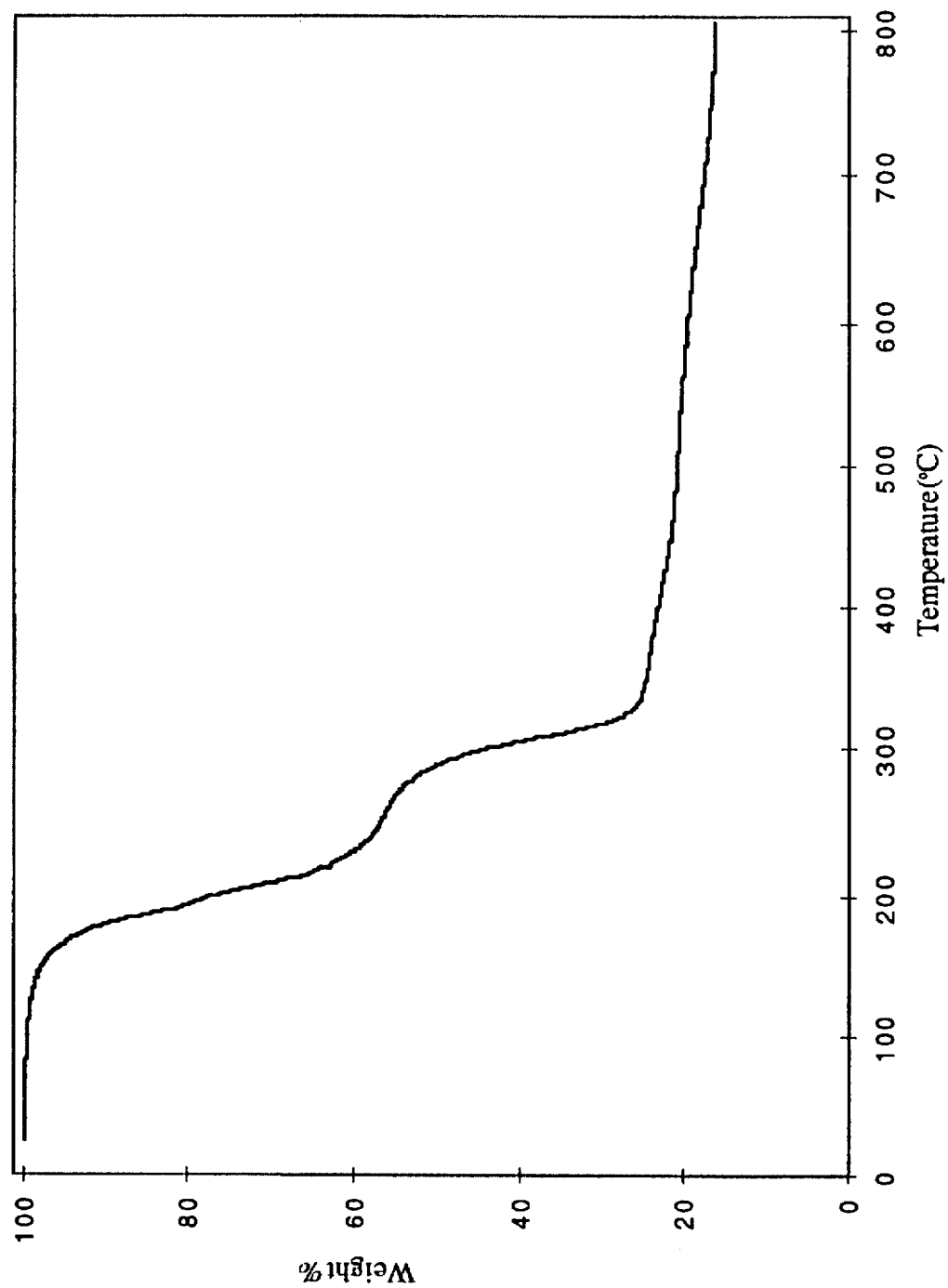
FIG. 2 shows a TGA of $Ca(SAc)_2 \cdot 15$-crown-5 in $N_2$ atmosphere.
Figure 3:
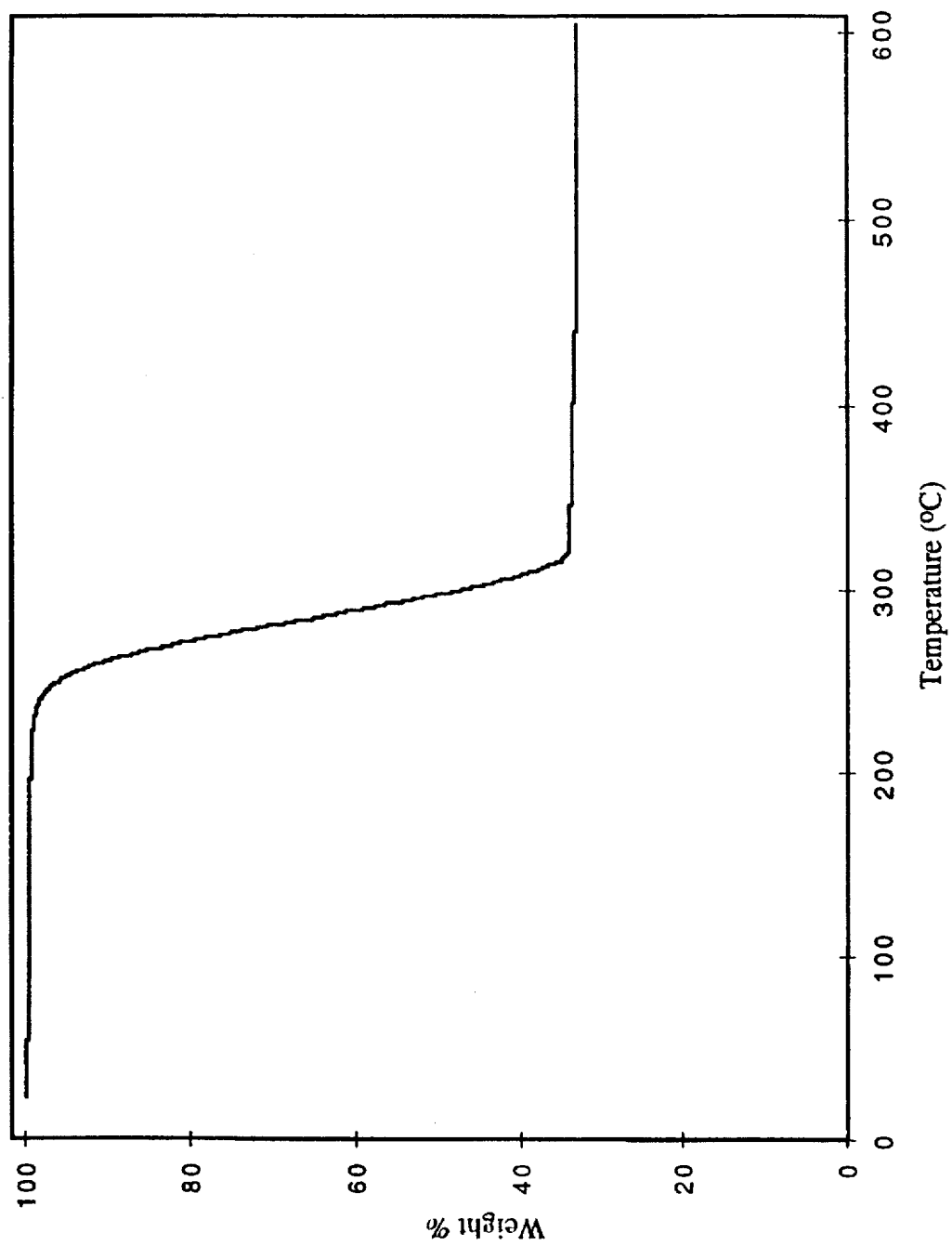
FIG. 3 shows a TGA of $Ba(SAc)_2 \cdot 18$-crown-6 in $N_2$ atmosphere.

The present invention will now be described in detail with the aid of several specific embodiments utilizing the FIGS. 1 through 15 and the Tables 1 through 4.

The invention describes the synthesis and characterization of a number of metal thioacetate compounds and their use in the formation of various metal sulfide films. First the synthesis and characterization of the compounds is described followed by the formation of metal sulfide films.

Synthesis of Group 2 Metal Compounds $M(SAc)_2 \cdot L$ with Crown Ether Ligands (L=15-crown-5, 18-crown-6, 12 crown-4)

(M=Ba, Ca, Sr)

Method 1) The reactions were carried out under nitrogen using Schlenk technique. To a 100 ml flask were added 7 mmol of $MH_2$, 7 mmol of L (L=15-crown-5, 18-crown6), 1.0 ml of HSAc (14 mmol) and 40 ml of dry THF. The solutions were stirred at room temperature (RT) for 12 hrs, followed by removal of the solvent under reduced pressure to leave a white solid. The crude products were recrystallized by slow addition of ether to an ethanol solution. $Sr(SAc)_2 \cdot 15$-crown-5 was obtained in 45% yield. Similar yields were obtained for the other compounds.

Method 2) The reactions were carried out under air. To a 100 ml beaker were added 7 mmol of $MCO_3$, 7 mmol of L (L=15-crown-5, 18-crown-6, 12-crown-4), 1.0 ml of HSAc (14 mmol) and 30 ml of distilled water. The clear solutions were stirred at RT to evaporate the water. The crude products were recrystallized by slow addition of ether to an ethanol solution. The crystals were kept under nitrogen atmosphere. The yields obtained were similar to method 1.

Characterization data of the prepared compounds are represented in Tables 1–3, wherein $L^1$=15-crown-5; $L^2$=18-crown-6; and L=12-crown-4.

TABLE 1

NMR Data

|  | $^1$H NMR/ppm (methanol-$d_4$) | | $^{13}$C NMR/ppm (methanol-$d_4$) | | |
| --- | --- | --- | --- | --- | --- |
|  | $CH_3$ | L | $CH_3$ | L | SC(O) |
| $Ca(SAc)_2 L^1$ | 2.41 | 3.78 | 38.4 | 70.1 | 222.2 |
| $Ca(SAc)_2 L^3$ | 2.41 | 3.77 | 38.8 | 69.2 | 222.5 |
| $Sr(SAc)_2 L^1$ | 2.40 | 3.83 | 38.5 | 69.7 | 221.4 |
| $Ba(SAc)_2 L^2$ | 2.39 | 3.78 | 38.8 | 71.3 | 221.0 |

TABLE 2

Elemental Analysis Data

|  | % C found | % C calc. | % H found | % H calc. |
| --- | --- | --- | --- | --- |
| $Ca(SAc)_2 L^1$ | 40.84 | 40.96 | 6.52 | 6.38 |
| $Ca(SAc)_2 L^3$ | 36.91 | 39.33 | 5.80 | 6.05 |
| $Sr(SAc)_2 L^1$ | 36.51 | 36.60 | 5.90 | 5.67 |
| $Ba(SAc)_2 L^2$ | 34.32 | 34.83 | 5.67 | 5.88 |

TABLE 3

IR Data for (C = O)/cm$^{-1}$

| $Ca(SAc)_2 L^1$ | 1542, 1516, 1637 |
| --- | --- |
| $Ca(SAc)_2 L^3$ | 1534, 1499 |
| $Sr(SAc)_2 L^1$ | 1549, 1527 |
| $Ba(SAc)_2 L^2$ | 1533 |

Determination of Molecular Structure of the Crown Ether Adducts

In order to determine the coordination of the thioacetate groups and the degree of oligomerization in the solid state, $Ca(SAc)_2 \cdot 15$-crown-5 was structurally characterized in the solid state by single crystal X-ray diffraction analysis. The X-ray diffraction analysis showed that in the solid state $Ca(SAc)_2 \cdot 15$crown-5 is monomeric (see FIG. 1). The calcium atom is eight-coordinate by binding to all oxygen atoms of the 15-crown-5 ring, the oxygen and sulfur of one chelated thioacetate and the oxygen of the other thioacetate ligand. The sulfur atom of the second thioacetate ligand dangles. It is not coordinated with the calcium atom and there is no evidence for intermolecular interaction to adjacent molecules. These data clearly demonstrate that this species is monomeric and likely to be soluble in organic solvents and suitable for chemical vapor deposition, in particular aerosol-assisted CVD.

Thermal Decomposition Studies (TGA) of $M(SAc)_2 \cdot L$ with M =Ca, Sr, Ba; L=15-crown-5, 18-crown-6, 12-crown-4

In general, thermal decomposition (thermogravimetric analysis=TGA) of $M(SAc)_2 \cdot L$ with M=Ca, Sr, Ba and L=15crown-4, 18-crown-6, and 12-crown-4 in air resulted in the loss of the polyether ligand and formation of the mixtures of the corresponding oxides, carbonates and sulfates. However, crystalline SrS was obtained in air at 600° C. Thermal decomposition in nitrogen resulted in the loss of the polyether ligand and formation of the corresponding crystalline metal sulfide at 300° C. The metal sulfide was easily oxidized to the metal sulfate at high temperatures even by small amounts of air, for example, in the case of BaS.

For $Ca(SAc)_2 \cdot 15$-crown-5 in nitrogen a two-step process (see FIG. 2) was observed. The respective weight losses can be attributed to the loss of 15-crown-5 and thioacetate anhydride $Ac_2S$.

For the Ba and Sr compounds (see FIG. 3) a one step process was observed. The total mass loss corresponds to the loss of polyether and $Ac_2S$. Metal sulfide was formed only in nitrogen at 600° C.

Figure 4:
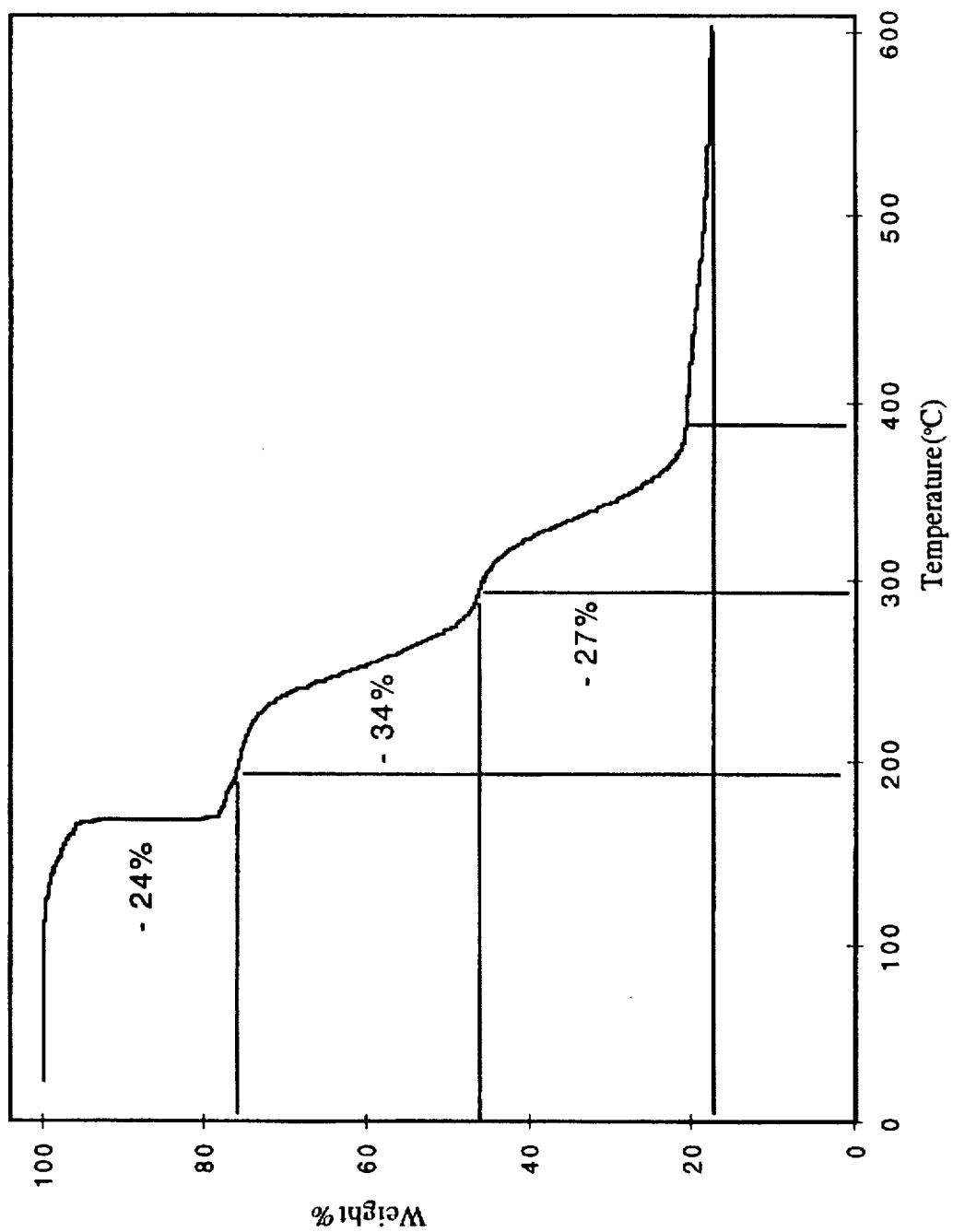
FIG. 4 shows a TGA of $Ca(SAc)_2 12$-crown-4 in $N_2$ atmosphere.
Figure 5:
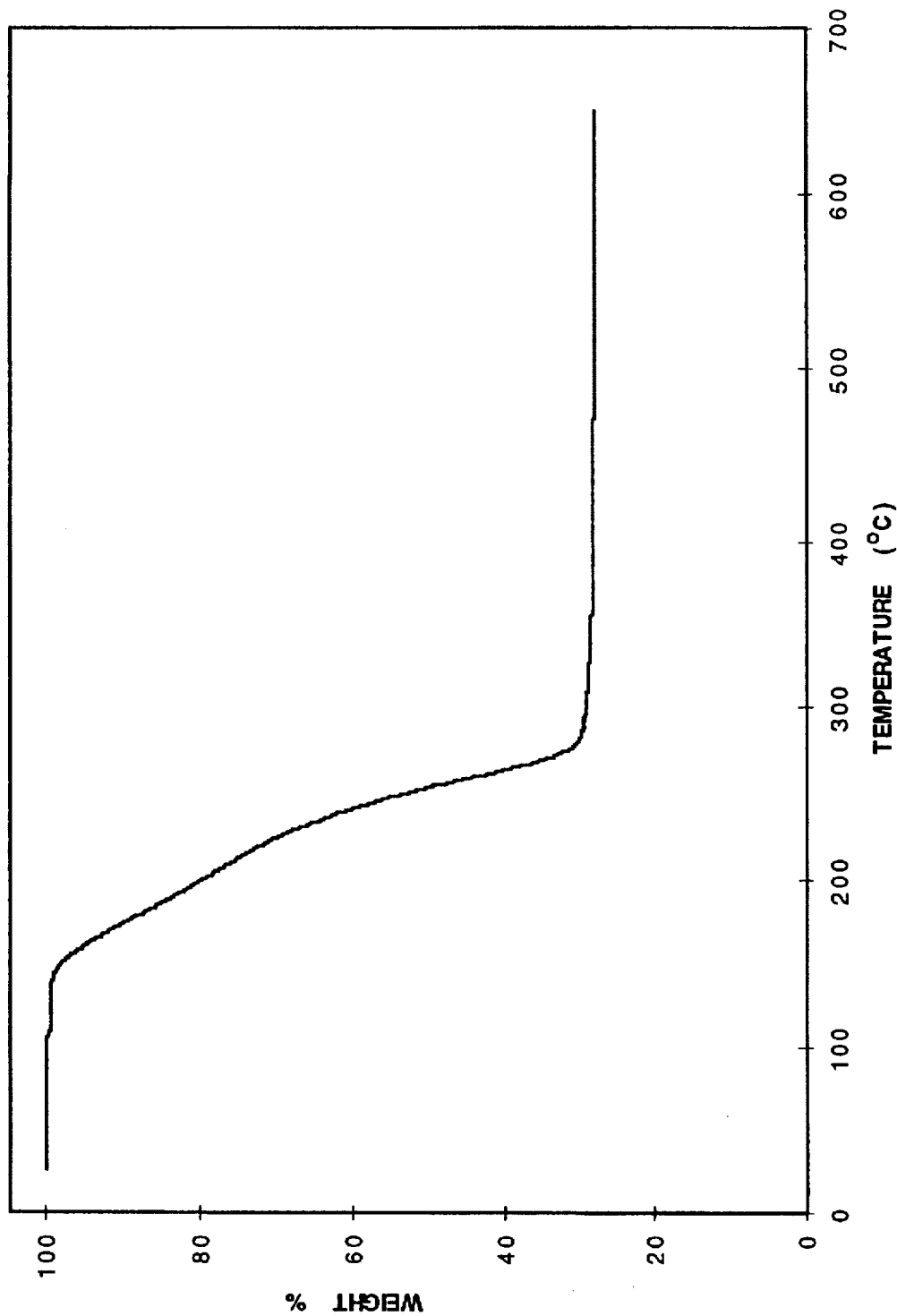
FIG. 5 shows a TGA of $Cd(SAc)_2 \cdot 18$-crown-6 in $N_2$ atmosphere.

The thermal composition of $Ca(SAc)_2 \cdot 12$-crown-4 in nitrogen differed from the decomposition process of $Ca(SAc)_2 \cdot 15$-crown-5 in nitrogen (see FIG. 4). A three-step process was observed for $Ca(SAc)_2 \cdot 15$-crown-5 and the final crystalline product was only CaS.

The results of the TGA experiments are compiled in Table 4.

TABLE 4

TGA Data

|  | air | | nitrogen | |
| --- | --- | --- | --- | --- |
|  | T/°C. | Cryst. Prod. | T/°C. | Cryst. Prod. |
| $Ca(SAc)_2 L^1$ | 900 | $CaSO_4$/CaO | 800 | CaS/CaO/Ca |
| $Ca(SAc)_2 L^3$ |  |  | 600 | CaS |
| $Sr(SAc)_2 L^1$ | 800 | $SrS/SrSO_4$ | 600 | SrS |
|  | 600 | SrS |  |  |
| $Ba(SAc)_2 L^2$ | 600 | $BaSO_4/BaCO_3$ | 900 | $BaSO_4$ |
|  |  |  | 600 | BaS |

$Ca(SOCMe)_2 \cdot THF$ 0.295 g (7 mmol) $CaH_2$ was stirred in 40 ml of THF at 0° C. and 1 ml (14 mmol) thioacetic acid was added. The solution was stirred for 12 hrs at RT. After filtration the resulting clear yellow solution was reduced in volume by evaporating the solvent in vacuum. A yellow crystalline powder was isolated. The final yield was 5.20 g (70.7%).

Elemental Analysis: Calc. for $C_8H_{14}O_3S_2Ca$ (MW 262.40): C: 36.62, H: 5.38; found: C: 35.97, H: 5.62.

¹H NMR (δ in ppm; CDCl₃): 1.84 (4H, t); 2.49 (6H, s); 3.82 (4H, t); (δ in ppm; C₆D₆): 1.34 (4H, t); 2.77 (6H, s); 3.69 (4H, t).

¹³C{¹H}-NMR (δ in ppm; CDCl₃): 25.4 (THF, s); 37.9 (H₃C-C(O)S, s); 68.9 (THF, s); 230.1 (H₃C-C(O)S, s).

¹³C CP-MAS-NMR (δ in ppm): 25.78 (THF, s); 38.08 (H₃C-C(O)S, s); 69.71 (THF, s); 230.80 (H₃C-C(O)S, s).

Ca(SOCMe)₂·2 PY 0.295 g (7 mmol) CaH₂ was stirred in 40 ml of Pyridine at 0° C. as 1 ml (14 mmol) thioacetic acid was added. The solution was stirred for 12 hrs at RT. After filtration the resulting clear yellow solution was reduced in volume by evaporating the solvent in vacuum. A colorless powder was isolated. The final yield was 48%.

Elemental Analysis: Calc. for C₁₄H₁₆O₂N₂S₂Ca (MW 348.49): C: 36.62; H: 5.38; found: C: 35.97; H: 5.62.

¹H NMR (δ in ppm; CD₃OD): 2.41 (6H, s); 7.43 (Py, m); 7.84 (Py, m); 8.53 (Py, m).

¹³C{¹H}-NMR (δ in ppm; CD₃OD): 38.2 (H₃C-C(O)S, s); 125.6 (Py, s); 138.4 (Py, s); 150.0 (Py, s); 222.7 (H₃C-C(O)SO, s).

Sr(SOCMe)₂·18-crown-6

To 1.033 g (7 mmol) SrCO₃ and 1.85 g (7 mmol) 18-crown-6, suspended in 30 ml distilled water, was added under stirring 1 ml (14 mmol) of thioacetic acid. The reaction was complete after CO₂ evolution had ceased (ca. 15 min). The slurry was stirred for 24 hrs to an almost colorless paste. The product was extracted with 30 ml ethanol and filtered. Colorless to pale yellow crystals were isolated by slow condensing of ether in a concentrated ethanol solution. The yield was 1.66 g (47%) and could be increased by collecting the second crystalline fraction from the supernatant.

Elemental Analysis: Calc. for C₁₆H₃₀O₈S₂Sr (MW 502.15): C: 38.27, H: 6.02; found: C: 37.86, H: 6.55.

¹H NMR (δ in ppm; CD₃OD): 2.40 (6H, s); 3.82 (24H, s).

¹³C{¹H}-NMR (δ in ppm; CD₃OD): 38.5 (H₃C-C(O)S, s); 71.2 (O-CH₂-CH₂-O, s); 221.6 (H₃C-C(O)S, s).

Sr(SOCMe)₂·15-crown-5

Synthesis and workup similar to Sr(SOCMe)₂·18-crown-6 has been employed. Colorless to pale yellow crystals were isolated. The final yield was 56%.

Elemental Analysis: Calc. for C₁₄H₂₆O₇S₂Sr (MW 458.10): C: 36.71, H: 5.72; found: C: 36.51, H: 5.90.

¹H NMR (δ in ppm; CD₃OD): 2.40 (6H, s); 3.83 (20H, s).

¹³C{H}-NMR (δ in ppm; CD₃OD): 38.5 (H₃C-C(O)S, s); 69.7 (O-CH₂-CH₂-O, s); 221.4 (H₃C-C(O)S, s).

IR: n(C=O) 1527.1549 cm⁻¹.

Ba(SOCMe)₂·15-crown-5

To 1.38 g (7 mmol) BaCO₃ and 1.39 ml (7 mmol) 15-crown-5, suspended in 40 ml distilled water, was added under stirring 1 ml (14 mmol) of thioacetic acid. The reaction was complete after CO₂ evolution had ceased (ca. 15 min). The slurry was stirred for 24 hrs to an almost colorless paste. The product was extracted with 40 ml ethanol and filtered. Colorless crystals were isolated by slow condensing of ether in a concentrated ethanol solution. The final yield was 2.54 g (71.5%).

Elemental Analysis: Calc. for C₁₄H₂₆O₇S₂Ba (MW 507.81): C: 33.11, H: 5.16; found: C: 33.01, H: 5.13.

¹H NMR (δ in ppm; CD₃OD): 2.40 (6H, s); 3.86 (20H, s).

¹³C{¹H}-NMR (δ in ppm; CD₃OD): 38.8 (H₃C-C(O)S, s); 69.9 (O-CH₂-CH₂-O, s); 221.1 (H₃C-C(O)S, s).

Ba(SOCMe)₂·18-crown-6·½H₂O

Synthesis and workup similar to Ba(SOCMe)₂·15-crown-5 was employed. Colorless crystals were isolated. The final yield was 76%.

Elemental Analysis: Calc. for C₁₆H₃₁O₈.₅S₂Ba (MW 560.87): C: 34.26, H: 5.57; found: C: 34.32, H: 5.67.

¹H NMR (δ in ppm; CD₃OD): 2.39 (6H, s); 3.78 (24H, s).

¹³C{¹H}-NMR (δ in ppm; CD₃OD): 38.8 (H₃C-C(O)S, s); 71.3 (O-CH₂-CH₂-O, s); 221.0 (H₃C-C(O)S, s).

IR: n(C=O) 1533 cm⁻¹.

Preparation of Group 12 Metal compounds

Cd(SAc)₂·18-crown-6

The reaction was carried out under air. To a 100 ml beaker were added 7 mmol of CdCO₃·7 mmol of 18-crown-6, 1.0 ml of HSAc (14 mmol) and 30 ml of distilled water. The clear solution was stirred at RT to evaporate the water. A pale yellow powder was obtained.

¹H NMR(methanol-d₄): 2.59 (s, 6H), 3.4 (s, 24H), 3.51 (s 8H).

¹³C NMR (methanol-d₄): 35.8 (s), 69.7 (s), 71.1 (s).

Figure 6:
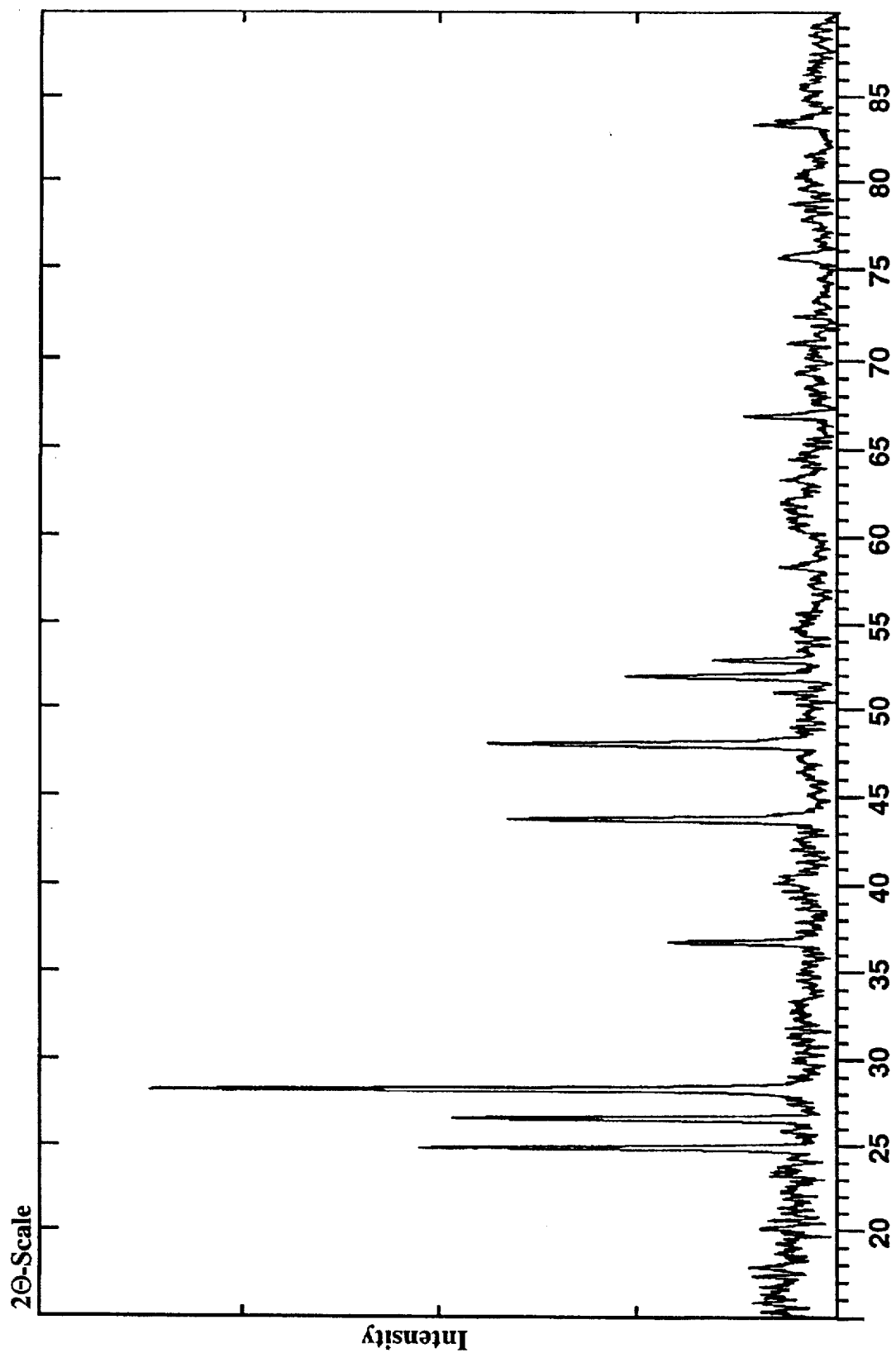
FIG. 6 shows powder X-ray diffraction data of CdS as formed by thermal decomposition of $Cd(SAc)_2 \cdot 18$-crown-6.

The thermal decomposition of Cd(SAc)₂·8-crown-6 (see FIG. 5) in nitrogen produced crystalline CdS (see FIG. 6). The total mass loss was 72 % corresponding to the loss of 18-crown-6 and the loss of thioacetate anhydride Ac₂S. The mass loss above 800° C. is due to the sublimation of CdS.

[(ᵗBuO)Cd(SOCMe)]₄

Method A): 1.79 g (3.4 mmol) Cd(SOCMe)₂·18-crown-6 and 0.88 g (3.4 mmol) Cd(OᵗBu)₂ were dissolved in 100 ml ether at RT. After 8 hrs the white slurry obtained was filtered and all volatiles removed under reduced pressure. The resulting white powder was recrystallized from toluene/hexane (1:4).

Method B): 1.32 g (5.1 mmol) Cd(OᵗBU)₂ were suspended in 130 ml ether. 0.39 g (5.1 mmol) thioacetic acid was added at RT and the reaction solution stirred for 2 hrs. Workup as described under method 1.

¹H NMR (δ in ppm; C₆D₆): 1.64 (9H, s); 2.23 (3H, s, J¹ᴴ⁻¹¹³/¹¹¹Cᵈ=6.3 Hz, 33% of th ¹³C{¹H}-NMR (δ in ppm; C₆D₆): 32.68 (H₃C-C(O)S, S, j¹³C⁻¹¹³/¹¹¹Cᵈ=51 Hz); 34.03 ((CH₃)₃-CO, s); 75.31 ((CH₃)₃-CO, s); 207.98 (H₃C-C(O)S,j¹³C⁻¹¹³/¹¹¹Cᵈ=34 Hz).

¹¹³Cd{¹H}-NMR (δ in ppm; C₆D₆): 202.76, s, j¹¹³ Cd-111Cd=34 Hz, 45% of the main signal.

Cd(SOCCH₃)₂TMEDA

Cadmium carbonate (1.00 g, 5.8 mmol)was placed in round-bottom flask with 25 mL toluene and 0.68 g (5.8 mmol) N, N, N, N-tetramethyl ethylenediamine. While stirring, 0.83 mL thioacetic acid was added (0.88 g, 11.6 mmol). An exothermic reaction took place immediately, as observed by CO₂ evolution. The mixture was stirred for 1 hour to obtain a toluene solution of Cd(SOCCH₃)₂TMEDA, and a yellowish precipitate containing a mixture of Cd(SOCCH₃)₂TMEDA, CdS, and other unidentified byproducts (decomposition of Cd(SOCCH₃)₂TMEDA to form CdS likely occurs by reaction with water produced in the reaction). The toluene solution was placed in the freezer and the product Cd(SOCCH₃)₂TMEDA crystallized out overnight as colorless blades. Yield: 1.00 g (45 % based on Cd).

Elemental analysis: Calculated 31.7% C, 5.8% H, 7.4% N; Found: 31.7% C, 5.4% H, 7.1% N.

TGA: The sample of Cd(SOCCH₃)₂TMEDA decomposed in one step around 200° C. with 38% wt. remaining (MW (CdS)/MW (Cd(SOCCH₃)₂TMEDA)×100=38%. The inorganic residue in the TGA pan was identified as hexagonal CdS by powder X-ray diffraction.

¹NMR data (C₆D₆): δ=1.79 (s, N₂(CH₃)₄C₂H₄, ³J¹¹¹,¹¹³Cd-¹-H =4.75 Hz) total integrated area of satellites with respect to main peak=25%, δ=2.03 (s, N₂(CH₃)₄C₂H₄, ³J¹¹¹,¹¹³ H=4.75 Hz) total integrated area of satellites with respect to main peak=25%, δ=2.45 (s, CH₃CSO).

$^{13}$C NMR data (C$_6$D$_6$): δ=34.54 (s, N$_2$(CH$_3$)$_4$C$_2$H$_4$), δ=46.26 (s, N$_2$(CH$_3$)$_4$C$_2$H$_4$), δ=56.61 (s, CH$_3$CSO), δ=250 (s, CH$_3$CSO).

$^{113}$Cd NMR data (C$_6$D$_6$): δ=346.4.

Figure 7:
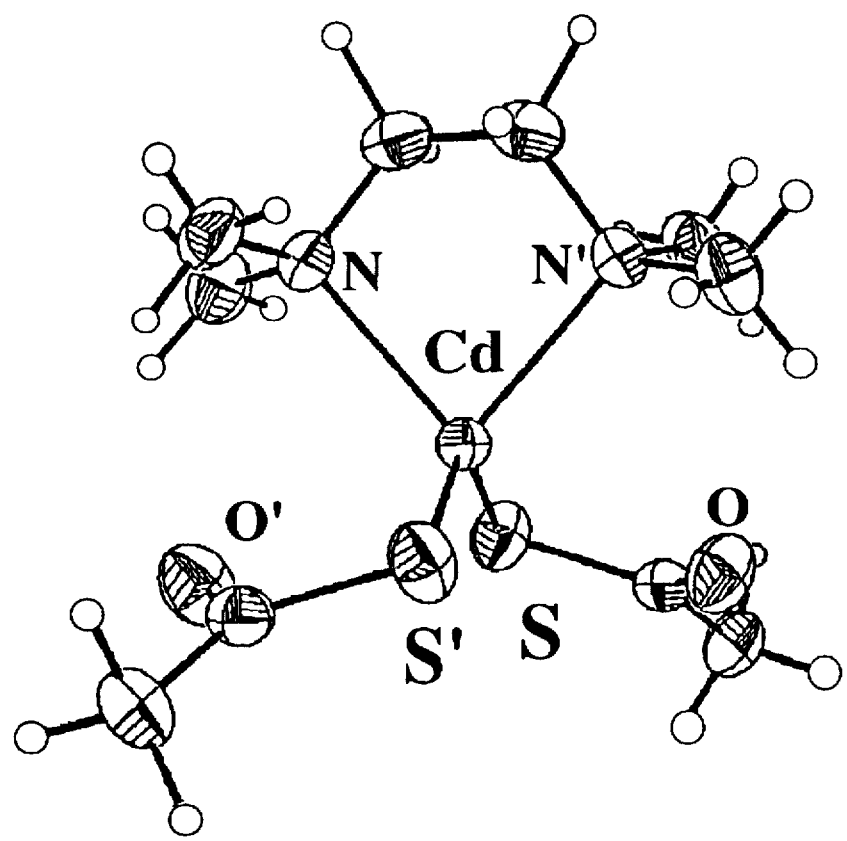
FIG. 7 shows the crystal structure of $Cd(SAc)_2 \cdot$TMEDA in the solid state.

The structure was determined by single crystal X-ray diffraction (see FIG. 7).

Zn(SOCCH$_3$)$_2$·TMEDA

Diethyl zinc (1 g, 8.1 mmol), 25 mL dry toluene and 0.94 g (8.1 mmol) N, N, N, N-tetramethyl ethylenediamine were combined in a round-bottom flask in an inert atmosphere box. The flask was removed from the box and placed in a dry ice-acetone bath. Thioacetic acid (1.16 mL, 16.2 mmol) was syringed into the flask while stirring. A white precipitate was formed immediately. The mixture was allowed to warm to RT and stirred for several hours. The mixture was then heated to 70° C. to allow most of the precipitate to dissolve, and the hot solution was immediately filtered. The product crystallized out of the solution as long colorless blades while standing at RT overnight. Yield: 2.5 g (93% based on Zn).

Elemental analysis: Calc: 36.2% C, 6.6% H, 8.4% N; Found: 36.12% C, 6.79% H, 8.34% N.

TGA: The sample of Zn(SOCCH$_3$)$_2$TMEDA decomposed in one step around 200° C. with 30% wt. remaining (MW (ZnS)/MW (Zn(SOCCH$_3$)$_2$TMEDA)×100=29%. The inorganic residue in the TGA pan was identified as poorly crystalline hexagonal or cubic ZnS by powder X-ray diffraction.

$^1$H NMR (C6D$_6$): δ=1.87 (s, N$_2$(CH$_3$)$_4$C$_2$H$_4$), δ=2.12 (s, N$_2$(CH3)$_4$C$_2$H$_4$), δ=2.45 (s, CH$_3$CSO).

$^{13}$C NMR: (C$_6$D$_6$): δ=35.66 (s, N$_2$(CH$_3$)$_4$C$_2$H$_4$), δ=46.60 (s, N$_2$(CH$_3$)$_4$C$_2$H$_4$), δ=56.61 (s, CH$_3$CSO), δ=250 (s, CH$_3$CSO).

Cd(SOCCH$_3$)$_2$Lu$_2$ (Lu=3,5-lutidine)

Cadmium carbonate (1 g, 5.80 mmol) and 3,5-lutidine (1.24 g, 11.60 mmol) and 20 mL toluene were combined in a round-bottom flask. Thioacetic acid (0.88 g, 11.60 mmol) was dropped into the mixture while stirring rapidly, and stirring was continued for 1 hour at RT. As the reaction proceeded, the solid cadmium carbonate disappeared, CO$_2$ bubble formation was observed and the resulting clear solution took on a yellow color. The toluene and volatile byproducts of the reaction (water) were removed under reduced pressure, and a white crystalline solid and a small amount of yellow cadmium sulfide remained. The solid was redissolved in toluene and filtered to remove the cadmium sulfide. The solution was placed in the freezer to yield colorless, blocky crystals. Yields ranged from 2.0 g–2.5 g (59%–74% based on Cd).

Elemental analysis: Calculated; 45.34% C, 5.04 % H and 5.88% N; found; 45.30% C, 5.14 %H and 5.68% N.

TGA: The sample of Cd(SOCCH$_3$)$_2$Lu$_2$ decomposed in one step around 150° C. with 32% wt. remaining (MW (CdS)/MW (Cd(SOCCH$_3$)$_2$Lu$_2$)×100=30%. The inorganic residue in the TGA pan was identified as hexagonal CdS by powder X-ray diffraction.

$^1$H NMR data (C$_6$D$_6$): 1.69 ppm [12H, CH$_3$-lutidine], 2.58 ppm [6H, SOCCH$_3$], 6.55 ppm [1H, lutidine para-CH], 8.50 ppm [2H, lutidine ortho-CH].

$^{13}$C NMR data: 17.8 ppm [CH$_3$-lutidine], 35.1 ppm [SOCCiH$_3$], 133.7 ppm [C-CH$_3$-lutidine], 138.8 ppm [para-CH-lutidine], 147.7 ppm [ortho CH-lutidine].

$^{113}$Cd NMR data: 353.5 ppm.

Figure 8:
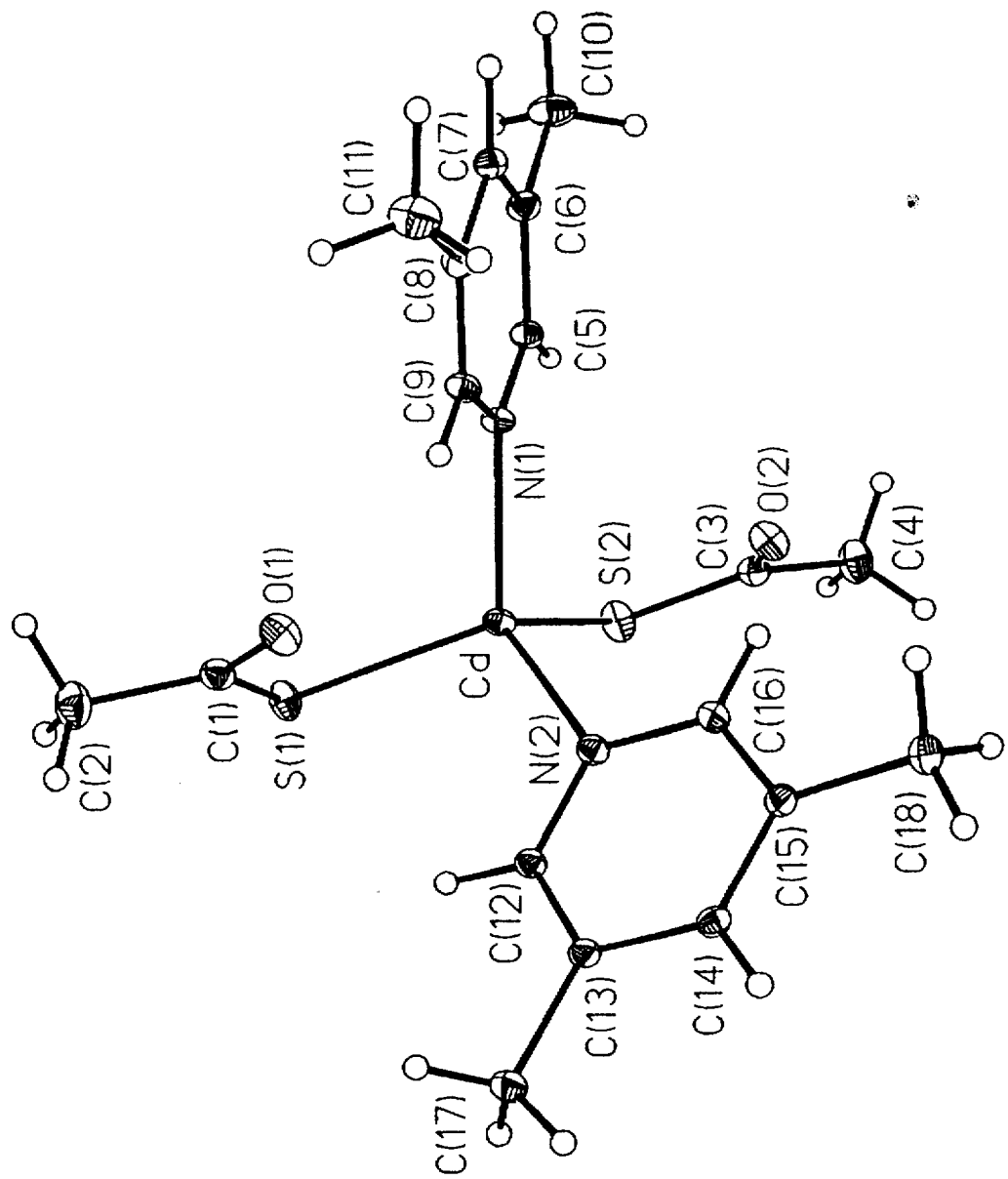
FIG. 8 shows the crystal structure of $3,5\text{-}Lu_2 \cdot Cd(SAC)_2$ in the solid state.

Single crystal X-ray diffraction was used to determine the structure of the compound (see FIG. 8).

Zn(SOCCH$_3$)$_2$Lu$_2$ (Lu=3,5-lutidine)

Diethyl zinc (1 g, 8.1 mmol), lutidine (1.73 g, 16.2 mmol) and 20 mL toluene were combined in a round-bottom flask in an inert atmosphere box. The flask was removed from the inert atmosphere box and placed in a dry ice-acetone bath. Thioacetic acid (1.16 mL, 16.2 mmol) was added to the solution via a pipette while stirring, and a white precipitation formed immediately. The solution was warmed to RT while stirring. After several hours, the solution was heated to 60° C. to dissolve most of the reaction product, and the hot solution was filtered immediately. The product crystallized at RT overnight as small colorless blocks. Yield: 2.7 grams (78% based on Zn).

Elemental analysis: Calculated: 50.3% C, 5.59% H and 6.52% N; found: 50.4% C, 5.70%H and 6.37% N.

TGA: The sample of Zn(SOCCH$_3$)$_2$Lu$_2$ decomposed in one step around 175° C. with 25% wt. remaining (MW (ZnS)/MW (Zn(SOCCH$_3$)$_2$Lu$_2$)×100=23%. The inorganic residue in the TGA pan was identified as poorly crystalline hexagonal or cubic ZnS by powder X-ray diffraction.

$^1$H NMR data (C$_6$D$_6$): 1.63 ppm [12H, CH$_3$-lutidine], 2.55 ppm [6H, SOCCH$_3$], 6.47 ppm [2H, lutidine para-CH], 8.78 ppm [4H, lutidine ortho-CH].

$^{13}$C NMR data: 17.8 ppm [CH$_3$-lutidine], 36.1 ppm [SOCCH$_3$], 134.3 ppm [C-CH$_3$-lutidine], 140.1 ppm [para-CH-lutidinel], 147.4 ppm [ortho CH-lutidine].

Figure 9:
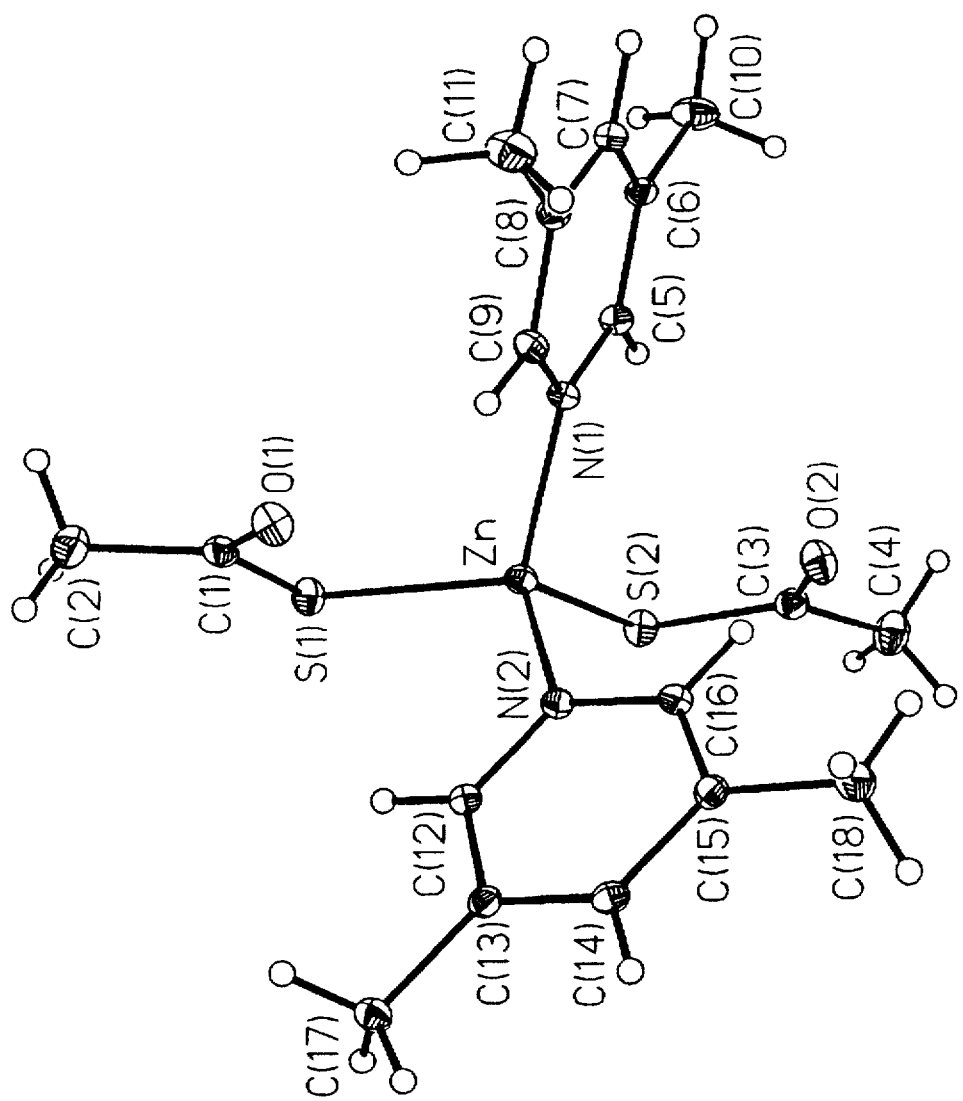
FIG. 9 shows the crystal structure of $3,5\text{-}Lu_2 \cdot Zn(SAc)_2$ in the solid state; p

Single crystal X-ray diffraction was used to determine the structure of the compound (see FIG. 9).

Cd(SOCC(CH$_3$)$_3$)$_2$TMEDA

Cadmium carbonate (1 g, 5.80 mmol) and TMEDA (0.673 g, 5.80 mmol) and 20 mL toluene were combined in a round-bottom flask. Thiopivalic acid (1.5 mL, 11.82 mmol) were dropped into the mixture while stirring rapidly. The reaction took place immediately, noted by the disappearance of the solid cadmium carbonate and CO$_2$ bubble formation. The resulting clear solution took on a yellow color. Since decomposition of the reaction product to CdS was observed after a few min., the reaction mixture was stirred for only 15 min. before filtering out the precipitate. The toluene and volatile byproducts of the reaction (water) were removed under reduced pressure, and a glassy, creamy solid remained. The solid was redissolved in pentane and crystallized as long colorless needles at 0° C. Yield: 2.2 g (82% based on Cd).

Elemental analysis: Calculated: 41.5% C, 7.35% H and 6.06% N; found: 41.33% C, 7.31% H and 5.95% N.

TGA: The sample of Cd(SOCC(CH$_3$)$_3$)$_2$TMEDA decomposed in one step around 150°–200° C. with 30% wt. remaining (MW (CdS)/MW (Cd(SOCC(CH$_3$)$_3$)$_2$TMEDA)× 100=31%. The inorganic residue in the TGA pan was identified as hexagonal CdS by powder X-ray diffraction.

$^1$H NMR data (C$_6$D$_6$): 1.39 ppm [18H, SOCC(CH$_3$)$_3$], 1.82 ppm [4H, C$_2$H$_4$-TMEDA, $^3$J-$^{113}$Cd-$^{111}$Cd=4.3 Hz (area of satellites =25% of major peak)], 2.05 ppm [12H, CH$_3$-TMEDA, $^3$J-$^{113}$Cd-$^{111}$Cd =4.5 Hz (area of satellites=25% of major peak)].

$^{13}$C NMR data: 29.5 ppm [SOCC(CH$_3$)$_3$], 46.2 ppm [CH$_3$-TMEDA], 47.3 ppm [SOCC(CH$_3$)$_3$], 56.7 ppm [C$_2$H$_4$-TMEDA]. $^{113}$Cd NMR: 335.6 ppm.

Cd(SOCC(CH$_3$)$_3$)$_2$-Lu$_2$ (Lu=3,5-lutidine)

Cadmium carbonate (1 g, 5.80 mmol) and lutidine (1.24 g, 11.60 mmol) and 20 mL toluene were combined in a round-bottom flask. Thiopivalic acid (1.5 mL, 11.82 mmol) were dropped into the mixture while stirring rapidly. The reaction took place slowly; after approximately 40 min., the solution become clear and yellow, and evolution of CO$_2$ was observed. Reaction was stirred for 2 more hours at RT. Toluene and volatile byproducts of the reaction (water) were removed under reduced pressure, and a glassy, white solid remained. The solid was redissolved in toluene and pentane was introduced slowly by gas phase diffusion. After 4 days, the product crystallized as long, colorless blades. Yield: 2.2 g (68% based on Cd).

Elemental analysis: Calculated: 51.4% C, 6.42% H and 5.00% N; found: 51.29% C, 6.60% H and 4.88% N.

TGA: The sample of $Cd(SOCC(CH_3)_3)_2Lu_2$ decomposed in one step around 150° C. with 27% wt. remaining (MW (CdS)/MW $(Cd(SOCC(CH_3)_3)_2Lu_2) \times 100 = 26\%$. The inorganic residue in the TGA pan was identified as well crystallized hexagonal CdS by powder X-ray diffraction.

$^1$H NMR data $(C_6D_6)$: 1.50 ppm [1 8H, $SOCC(CH_3)_3$], 1.65 ppm [12H, $CH_3$-lutidine], 6.47 ppm [2H, lutidine para-CH], 8.53 ppm [4H, lutidine ortho-CH].

$^{13}$C NMR data: 17.8 ppm [$CH_3$-lutidine], 29.6 ppm [$SOCC(CH_3)_3$], 47.9 ppm [$SOCC(CH_3)_3$], 134.0 [$C$-$CH_3$-lutidine], 138.4 ppm [para-CH-lutidine], 147.5 ppm [ortho CH-lutidine].

$^{113}$Cd NMR data: 338.6 ppm.

$Zn(SOCC(CH_3)_3)_2Lu_2$

Diethyl zinc (1 g, 8.1 mmol), lutidine (1.73 g, 16.2 mmol) and 20 mL toluene were combined in a round-bottom flask in an inert atmosphere box. The flask was removed from the inert atmosphere box and placed in a dry ice-acetone bath. Thiopivalic acid (2.06 mL, 16.2 mmol) was added to the solution via a pipette while stirring. The pale yellow solution was warmed to RT while stirring for several hours, and placed in a freezer for crystallization. Large, blocky colorless crystals formed overnight.

Elemental analysis: Calculated: 56.1% C, 7.01% H and 5.45% N; found: 56.09% C, 7.12% H and 5.37% N.

TGA: The sample of $Zn(SOCC(CH_3)_3)_2Lu_2$ decomposed in one step around 200° C. with 20% wt. remaining (MW (CdS)/MW $(Cd(SOCC(CH_3)_3)_2Lu_2) \times 100 = 19\%$. The inorganic residue in the TGA pan was identified as poorly crystalline hexagonal or cubic ZnS by powder X-ray diffraction.

$^1$H NMR data $(C_6D_6)$: 1.40 ppm [18H, $SOCC(CH_3)_3$], 1.65 ppm [12H, $CH_3$-lutidine], 6.51 ppm [2H, lutidine para-CH], 8.69 ppm [4H, lutidine ortho-CH].

$^{13}$C NMR data: 17.8 ppm [$CH_3$-lutidine], 29.3 ppm [$SOCC(CH_3)_3$], 48.2 ppm [$SOCC(CH_3)_3$], 134.02 [$C$-$CH_3$-lutidine], 140.1 ppm [para-CH-lutidine], 147.3 ppm [ortho CH-lutidine].

Figure 10:
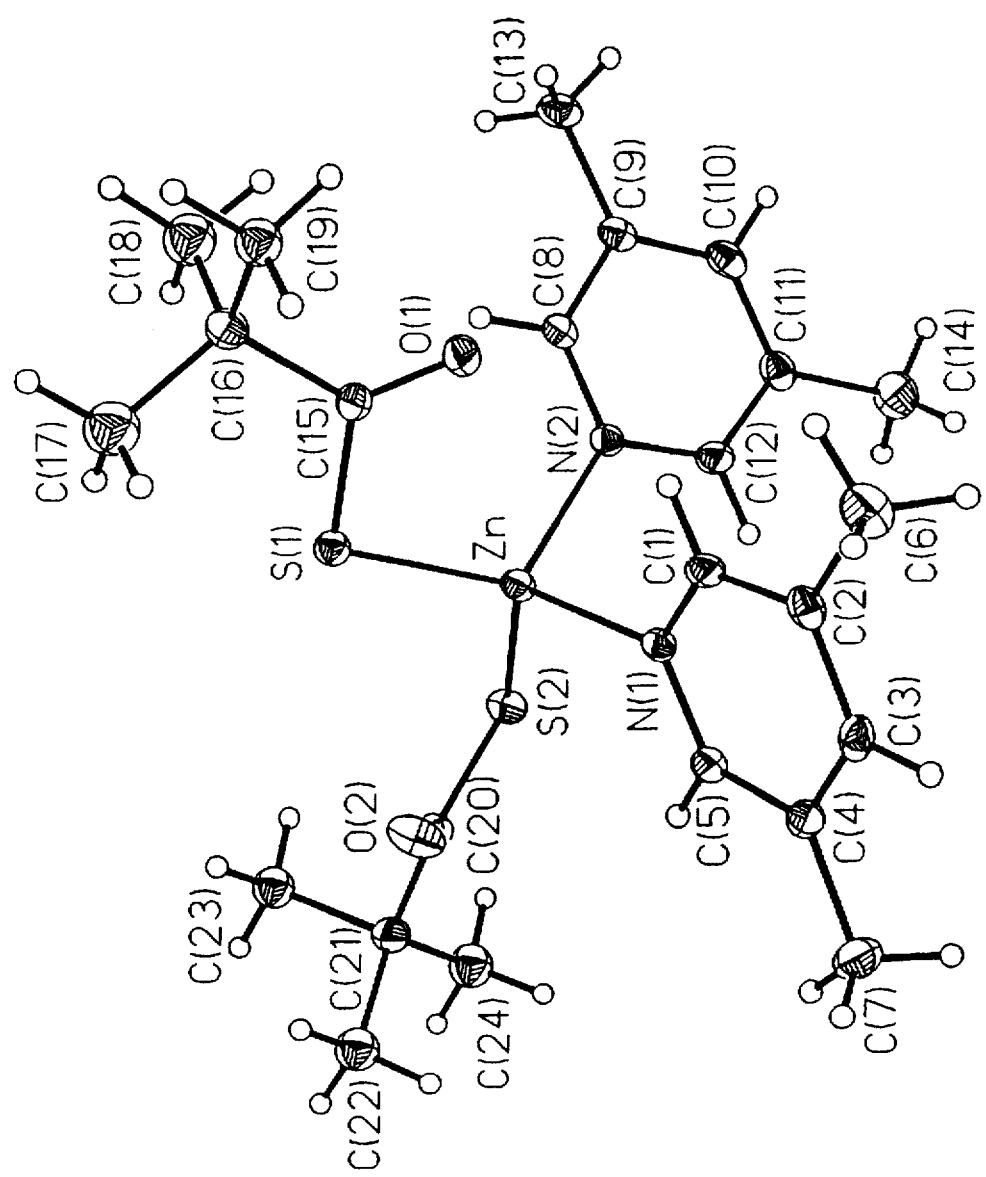
FIG. 10 shows the crystal structure of $Zn(SOCC(CH_3)_3)_2Lu_2$ in the solid state.

Single crystal x-ray diffraction was performed to determine the structure (see FIG. 10).

$Cd(SOCMe)_2 \cdot 18$-crown-6

2 ml (28 mmol) thioacetic acid were added to a suspension of 2.42 g (14 mmol) $CdCO_3$ and 3.70 g (14 mmol) 18-crown-6 in 50 ml water. After stirring for 24 hrs most of the $H_2O$ had evaporated. The product was extracted with 150 ml ethanol. Hot filtering produced a colorless filtrate. The solvent was removed under reduced pressure to give colorless crystals. Yield: 6.2 g (84%).

Elemental Analysis: Calc. for $C_{16}H_{30}O_8S_2Cd$ (MW 526.94): C: 36.47, H: 5.74; found: C: 36.34; H: 6.14.

$^1$H NMR (δ in ppm; $CD_3OD$): 2.39 (6H, s); 3.64 (24H, s); (δ in ppm); $C_6D_6$): 2.59 (6H, s); 3.47 (24H, s).

$^{13}C\{^1H\}$-NMR (δ in ppm; $C_6D_6$): 35.8 ($H_3C$-C(O)S, s); 69.7 (O-($CH_2$-$CH_2$-O, s); 225.0 ($H_3C$-C(O)S, s).

$^{113}Cd\{^1H\}$-NMR (δ in ppm; $C_6D_6$): 115.38 (s). $^{13}$C CP-MAS-NMR (d (ppm): 37.21 (s); 70.73 (s, br); 203.38 (s); 204.09 (s).

Synthesis of Group 13 Metal Compounds $[In(SOCMe)_4]^+[HNC_5H_3Me_2]$

To a clear benzene solution of $InEt_3$ (2.019 g, 0.001 Mol) in a glove box, an excess of thioacetic acid (3.245 g, 0.043 Mol) was added dropwise, slowly, and gas evolution was observed. To the above reaction solution, 2.0 mL of 3,5-dimethyl pyridine was dropped in to form a light yellow clear solution. The final light yellow clear solution was stirred for one day at RT under a nitrogen atmosphere. After the solvent was pumped out, a light yellow oily residue was formed. To this residue, 10.0 mL fresh benzene and 5 mL pentane were added and upon storing this solution in refrigerator at $-5°$ C. for one day, the clear plate-shape crystals formed. After filtration, washing with pentane and pumping dry, 4.08g (78% yield) final product was obtained.

$^1$H NMR(250 MHz, 20° C., pyridine-$d_5$): 2.12 ppm (s, 6H $CH_3$ of 3,5-dimethyl pyridine), 2.39 ppm (s, 12H, $CH_3$ of $In(SCOCH_3)_4$), 7.18 ppm (s, 1H, 3,5-dimethyl pyridine), 8.40 ppm (s, 2H, 3,5-dimethyl pyridine).

$^{13}$C NMR (63 MHz, 20° C., pyridine-$d_5$): 18.06 ppm (s, $CH_3$ of 3,5-dimethyl pyridine), 34.31 ppm (s, $CH_3$ of In-$SCOCH_3$), 132.92 ppm (s, 3,5-dimethyl pyridine), 137.43 ppm (s, 3,5-dimethyl pyridine), 147.69 ppm (s, 3,5-dimethyl pyridine), 205.54 ppm (s, CO of In-$SCOCH_3$).

Elemental analysis: Calc. for $InC_{15}H_{22}O_4S_4N$: C: 34.40, H: 4.20, N: 2.68. Found: C: 34.65, H: 4.20, N: 2.96.

Figure 11:
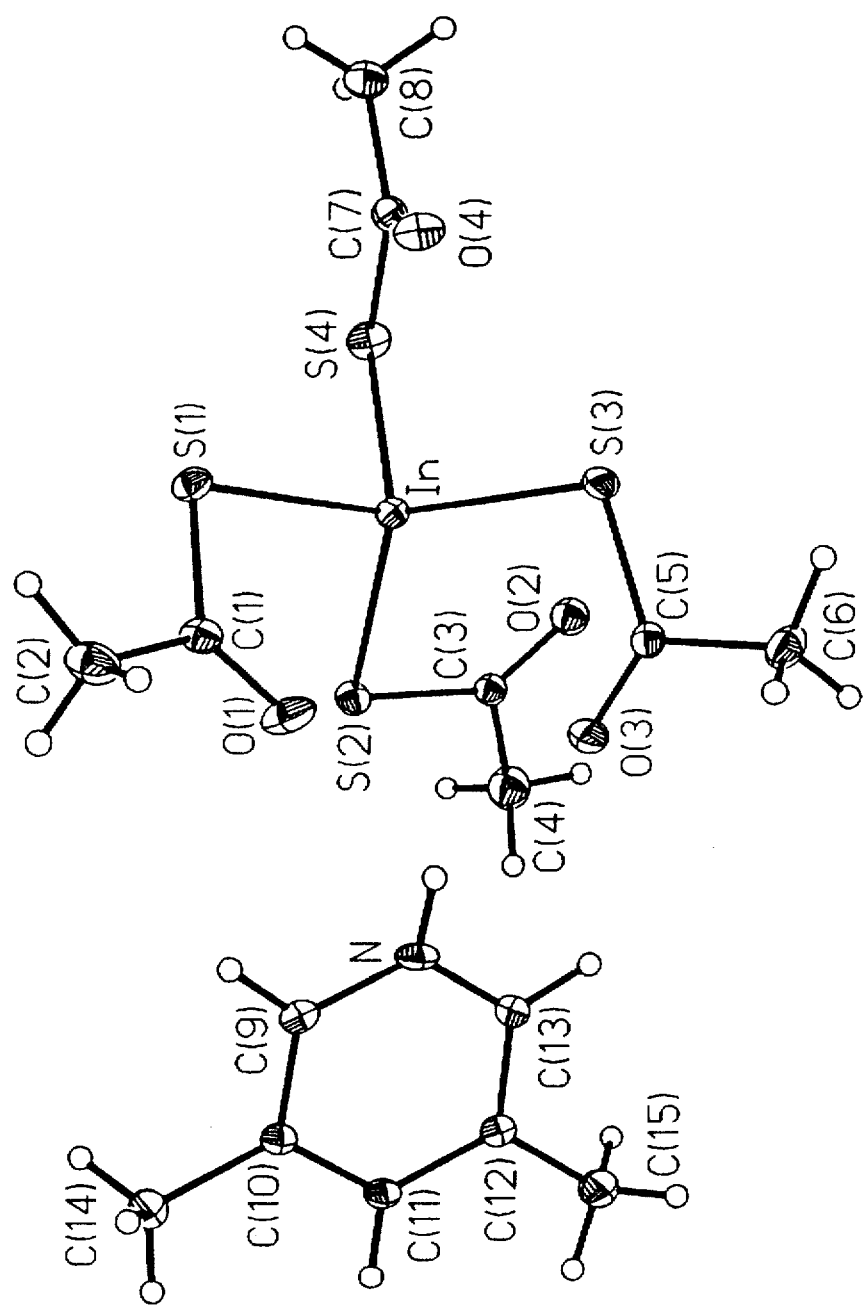
FIG. 11 shows the crystal structure of $3,5\text{-}Lu \cdot In(SAc)_4$ in the solid state.

Single crystal X-ray diffraction was performed and the structure was solved by the Patterson method. SHELXL software used for all computations. (G. Sheldrick, Siemens, XRD, Madison, Wis., USA). The structure of this compound is shown in FIG. 11.

Synthesis of $LGa(SCOCH_3)_2Me$

To a clear toluene solution of $GaMe_3$ (0.576 g, 0.005 mol) in a glove box, thioacetic acid (1.15 g, 0.015 mol) was added dropwise slowly to form a light yellow clear solution. The release of gas bubbles was observed. To the above reaction solution, 1.0 mL of 3,5-dimethyl pyridine was dropped in. The final light yellow clear solution was stirred for one day at RT under a nitrogen atmosphere. After the solvent was pumped out, a light orange oily residue was formed. To this residue, 7.0 mL fresh pentane was added and upon storing this pentane solution at RT for one day, clear plate-shape crystals formed. After filtration, washing with pentane and pumping dry, 1.2 g final product was obtained (yield: 70%).

$^1$H NMR (250 MHz, 20° C., benzene-$d_6$): 0.97 ppm (s, 3H, Ga-$CH_3$), 1.47 ppm (s,6H, $CH_3$ of 3,5-dimethyl pyridine), 2.19 ppm (s, 6H, $CH_3$ of $Ga(SCOCH_3)_2$), 6.31 ppm (s, 1H, 3,5-dimethyl pyridine, 8.55 ppm (s, 2H, 3,5-dimethyl pyridine).

$^{13}$C NMR (63 MHz, 20° C., benzene-$d_6$): −4.22 ppm (s, $CH_3$ of Ga-$CH_3$), 17.62 ppm (s, $CH_3$ of 3,5-dimethyl pyridine), 34.82 ppm (s, $CH_3$ of Ga-SC(O)$CH_3$), 135.17 ppm (s, 3,5-dimethyl pyridine), 141.85 ppm (s, 3,5-dimethyl pyridine), 144.85 ppm (s, 3,5-dimethyl pyridine), 201.95 ppm (s, C(O) of Ga-SC(O)$CH_3$).

Elemental analysis: Calc. for $C_{12}H_{18}GaNO_2S_2$: C: 42.14, H: 5.27, N: 4.09. Found: C: 41.78, H: 5.41, N: 3.88.

Figure 12:
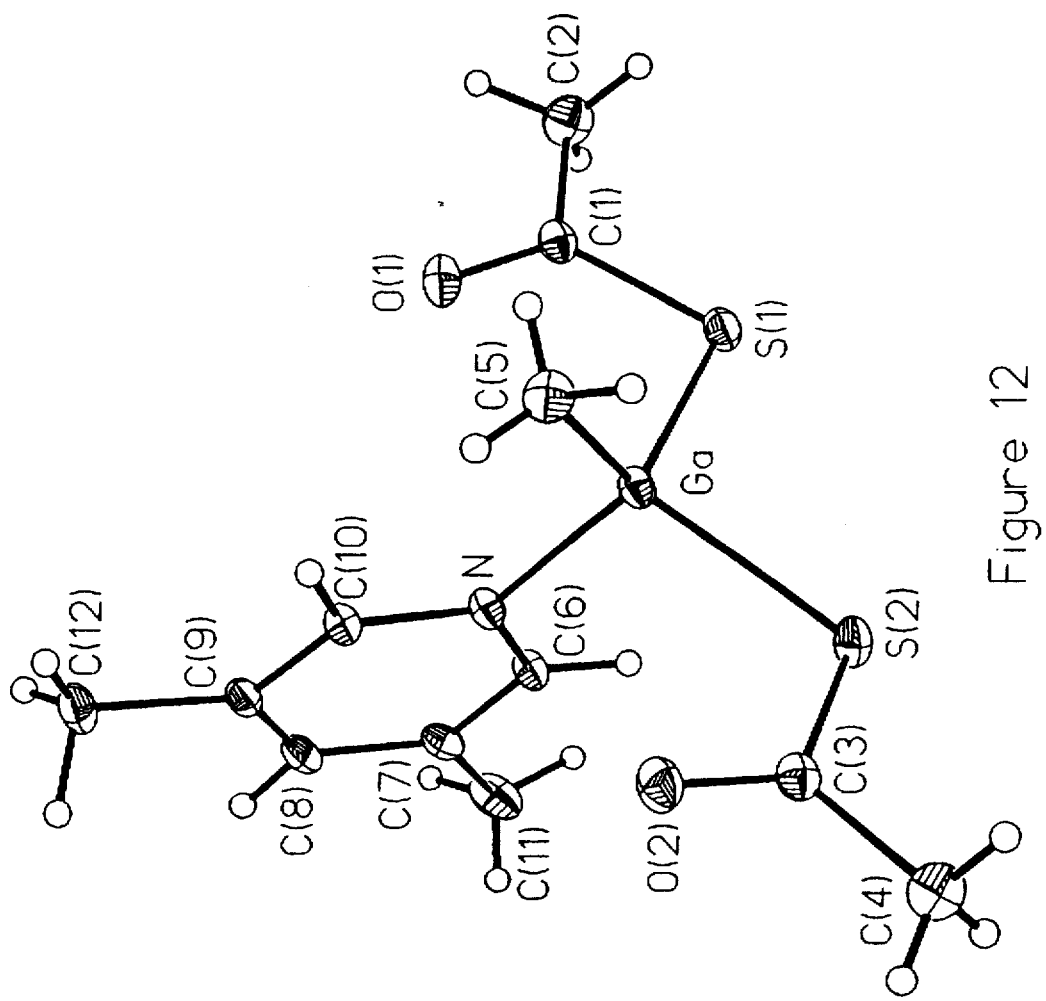
FIG. 12 shows the crystal structure of $3,5\text{-}Lu \cdot Ga(SAc)_2 (CH_3)$ in the solid state.

Single crystal X-ray diffraction was performed and the structure was solved by the Patterson method. SHELXL software used for all computations. (G. Sheldrick, Siemens, XRD, Madison, Wis., USA). FIG. 12 shows the structure of $LGa(SCOCH_3)_2(CH_3)$.

Synthesis of $LGa(SCOCH_3)_3$

The reaction was were carried out under a nitrogen atmosphere with dried and deoxygenated solvents. Triethyl gallium was used as purchased from Strem. Thioacetic acid (Aldrich) was purified by distillation.

The reaction was performed as described above for the synthesis of $LGa(SCOCH_3)_2Me$, except that recrystallization was achieved in the mixed solvents of benzene and pentane at 5° C. for 3 days. The final yield was 56% (1.12 g).

$^1$H NMR (250 MHz, 20° C., benzene-d$_6$): 1.52 ppm (s, 6H, CH$_3$ of 3,5-dimethyl pyridine), 2.13 ppm (s, 9H, CH$_3$ of Ga(SCOCH$_3$)$_3$)$_3$), 6.36 ppm (s, 1H, 3,5-dimethyl pyridine), 8.80 ppm (s, 2H, 3,5dimethyl pyridine).

$^{13}$C NMR (63 MHz, 20° C., benzene-d$_6$): 17.70 ppm (s, CH$_3$ of 3,5-dimethyl pyridine), 34.27 ppm (s, CH$_3$ of Ga-SCOCH$_3$), 135.46 ppm (s, 3,5-dimethyl pyridine), 142.71 ppm (s, 3,5-dimethyl pyridine), 145.11 ppm (s, 3,5-dimethyl pyridine), 200.48 ppm (s, C(O) of Ga-SC(O)CH$_3$).

Elemental analysis: Calc. for C$_{13}$H$_{18}$O$_3$S$_3$NGa: C: 38.83, H: 4.48, N: 3.48; Found: C: 38.70, H: 4.58, N: 3.41.

Preparation of [PySGa(SCOCH$_3$)$_3$·Py

The reaction was carried out under a nitrogen atmosphere with dried and deoxygenated solvents. Triethyl gallium was used as purchased from Strem. Thioacetic acid (Aldrich) was purified by distillation.

To a clear pentane solution of triethyl gallium (1.566 g, 0.01 mol) in a glove box, thioacetic acid (2.290 g, 0.003 mol) was added dropwise slowly. Upon addition of 15-crown-5 (2.390 g, 0.01 mol) to the reaction solution, a light yellow solid formed immediately. After stirring for 30 more min. in the glove box, the reaction flask was connected to a Schlenk line and was stirred at RT for 1 day. The crude yellow solid was filtered, washed with more fresh pentane and pumped dry. For recrystallization the above crude light yellow solid was then dissolved in 15 mL pyridine and left in a freezer at −30° C. The yield of final crystals was 1.5 g (53.2%).

$^1$H NMR (250 MHz, 20° C., Benzene-d$_6$): 2.08 ppm (s, br. 9H, Ga(SOCCH$_3$)), 6.52 ppm (s, 8H, Py), 6.80 ppm (s, 4H, Py), 8.90 ppm (s, 8H, Py).

$^{13}$C NMR (63 MHz, 20° C., benzene-d$_6$): 34.17 ppm (s) &34.57 ppm(s, CH$_3$of Ga(SCOCH$_3$)), 124.03 ppm(s, Py), 137.56 ppm(s, Py), 149.19 ppm(s, Py), 199.73 ppm (s, CO of Ga(SCOCH$_3$)).

Elemental Analysis: Calc. for [PySGa(SCOCH$_3$)]$_3$·Py: C: 36.90, H: 3.43, N: 6.62. Found: C: 37.56, H: 3.99, N: 6.49.

Figure 13:
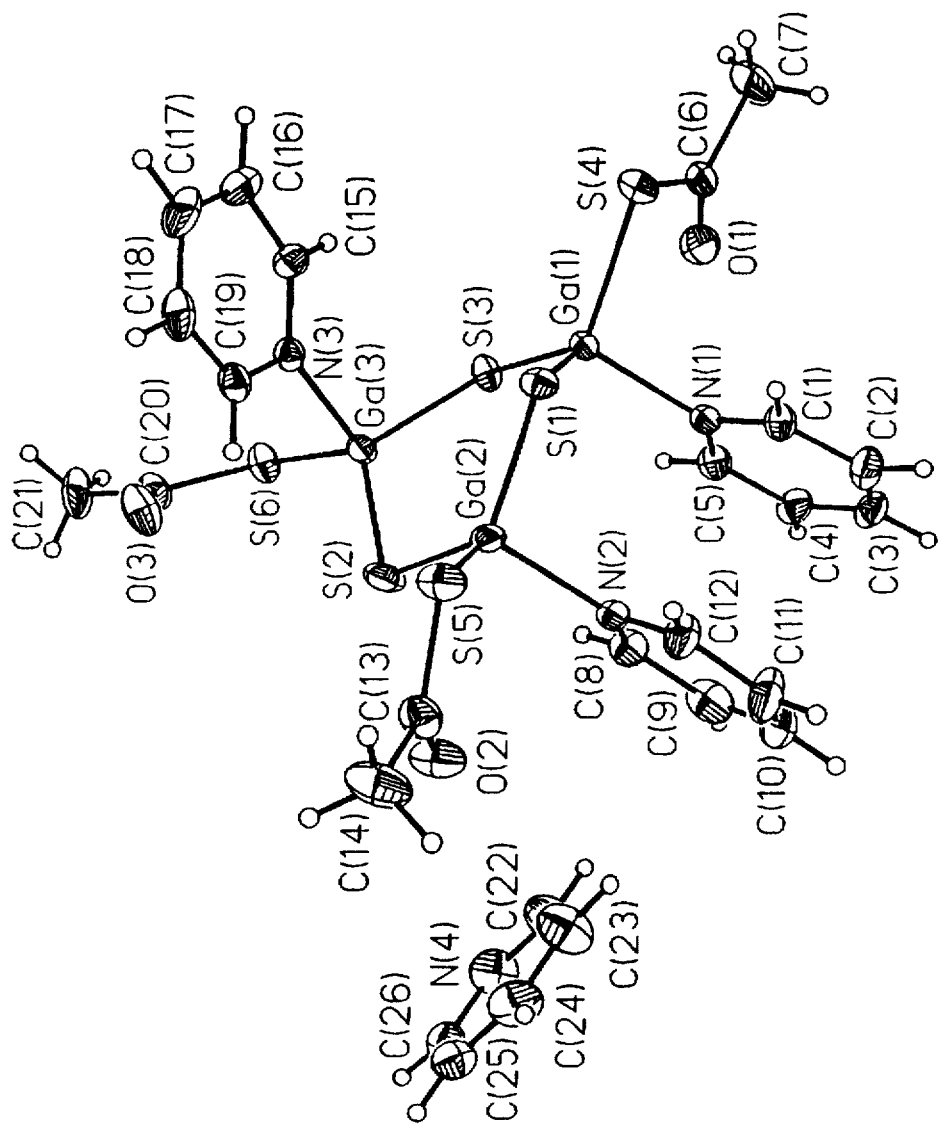
FIG. 13 shows the crystal structure of $[PySGa(SAc)]_3 \cdot Py$ in the solid state.

Single-crystal X-ray diffraction was performed and the structure was solved by the Patterson Method. SHELXL software used for all computations. (G. Sheldrick, Siemens XRD, Madison, Wis., USA). FIG. 13 shows the structure of [PySGa(SCOCH$_3$)]$_3$·Py.

Synthesis and Characterization of Group 14 Metal Compounds [(${}^t$BuO)Sn(SOCMe)]$_2$ 1.04 g (1.96 mmol) [Sn(O${}^t$Bu)$_2$]$_2$ were dissolved in 50 ml ether. 0.299 g (3.92 mmol) thioacetic acid was added at RT and the reaction solution stirred for 10 min. Immediate filtration resulted in a colorless solution. The volatiles were removed under vacuum and a colorless powder was obtained. Crystals could be grown in an ether solution at −30° C.

$^1$H NMR (δ in ppm; C$_6$D$_6$): 1.28 (9H, s); 2.25 (3H, s).

$^{13}$C{$^1$H}-NMR (δ in ppm; C$_6$D$_6$): 32.02 ((CH$_3$)$_3$-CO,s, J$^{136-117/Msn3}$C$^{117-119Sn}$=21 Hz, 55% of the main signal); 35.97 (H$_3$C-C(O)S, S); 76.89 ((CH$_3$)$_3$—CO, s); 211.0 (H$_3$C-C(O)S, s).

$^{119}$Sn{$^1$H}-NMR (δ in ppm: C$_6$D$_6$): −70.11, s, J$^{119Sn-117Sn}$=80 Hz, 9.5% of the main signal.

Preparation of Pb(SAc)$_2$·18-crown-6

Method a): The reaction was carried out in nitrogen and in the absence of light. In a 200 ml Schlenk flask were added 1.95 g of PbCl$_2$, 1.6 g of KSAc, 1.85 g of 18-crown-6 and 50 ml THF. The solution was stirred for 12 h at RT, followed by the removal of the solvent under reduced pressure to leave a white solid with brown impurities. The crude product was recrystallized from an ethanol solution. Colorless crystals with brown impurities were formed.

Method b): The reaction was carried out under air. To a 100 ml beaker were added 7 mmol of PbCO$_3$, 7 mmol of 18-crown-6, 1.0 ml of HSAc (14 mmol) and 30 ml of distilled water. Crystalline PbS was obtained after stirring for several hours.

$^1$H NMR (methanol-d$_4$) of the crude product: 2.32 (s, 6H), 3.63 (s, 24H); $^{13}$C NMR (methanol-d$_4$): 35.8 (s), 69.7 (s), 71.1 (s); $^1$H NMR(methanol-d$_4$) of the recrystallized product: 2.32 (s, 6H), 3.63 (s, 24H).

Figure 14:
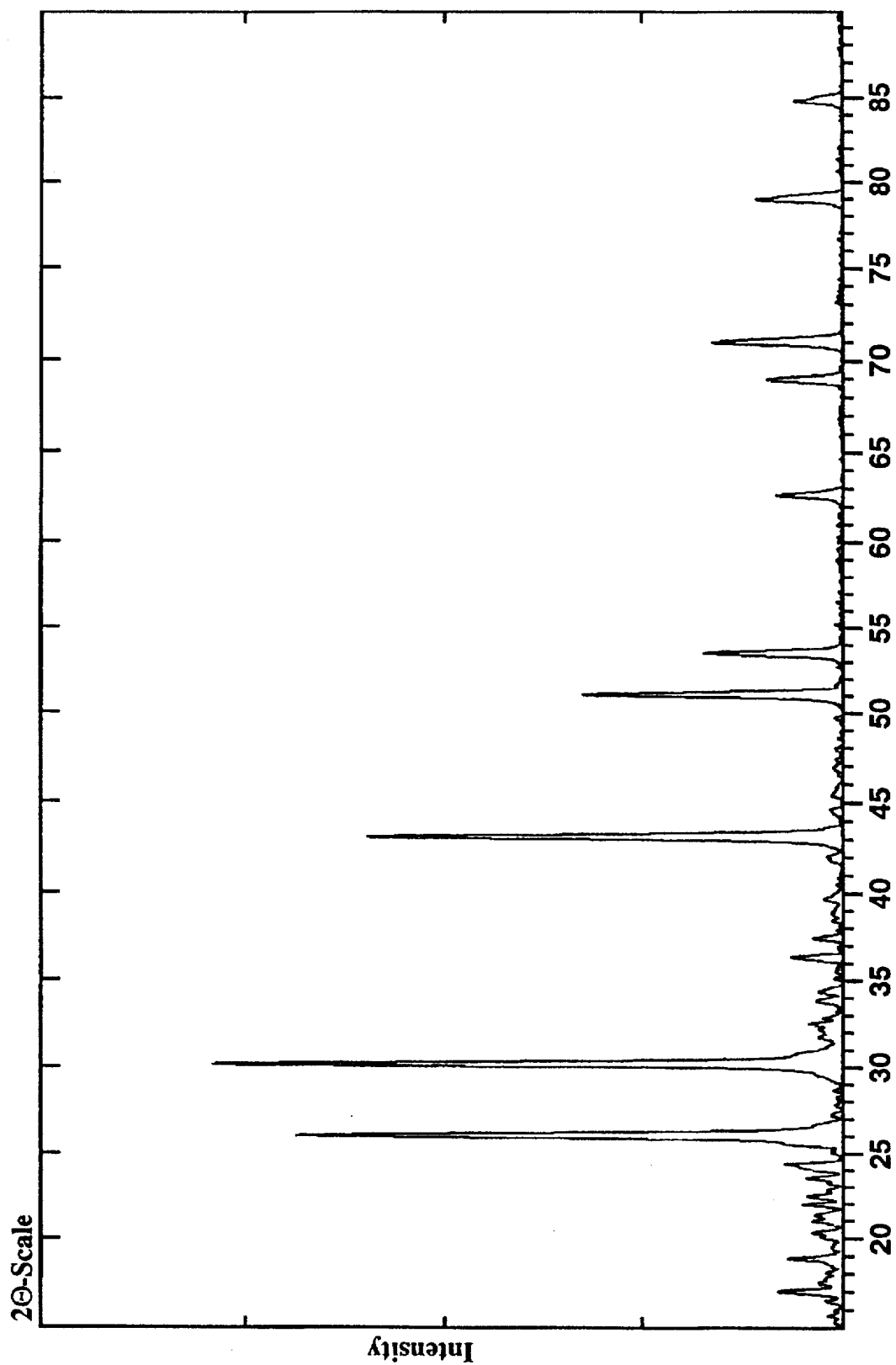
FIG. 14 shows powder X-ray diffraction data of PbS as formed by thermal decomposition of $Pb(SAc)_2 \cdot 18$-crown-6.

The thermal decomposition of Pb(SAc)$_2$·18-crown-6 in nitrogen produced crystalline PbS (see powder X-ray diffraction analysis of FIG. 14).

[Pb(SOCMe)·18-crown-6]$^{+[Pb(SOCMe)}{}_3^-]$ 1.87 g (7 mmol) PbCO$_3$ and 1.85 g (7 mmol) 18-crown-6 were suspended in 40 ml of dist. water. 1 ml (14 mmol) thioacetic acid was added through a pipette under the solution surface to avoid possible formation of brownish black impurities. After the evolution of CO$_2$ had ceased (ca. 5 min.), the solution was stirred for an additional 20 min. The product was collected on filter paper by filtering through a Buchner funnel. It was washed with 5 ml H$_2$O five times. After drying under vacuum the yield of the crude crystalline product was 2.73 g (80% based on 18-crown-6). Colorless needles were isolated by recrystallization from ethanol. The final yield was 2.38 g (69.4%).

Elemental Analysis: Calc. for C$_{20}$H$_{36}$O$_{10}$S$_4$Pb$_2$ (MW 979.14): C: 24.53, H: 3.71, found: C: 24.43, H: 3.91.

$^1$H NMR (δ in ppm; CD$_3$OD): 2.33 (12H, s); 3.80 (24, s).

$^{13}$C{$^1$H}-NMR (δ in ppm; CD$_3$OD): 39.0 (H$_3$C-C(O)S, s); 71.5 (O-CH$_2$-CH$_2$-O, s); 215.6 (H$_3$C-C(O)S, s).

Deposition of Metal Sulfide Films

The liquid-phase coating experiments were carried out as follows. The respective precursor was dissolved in ethanol to give a 1% to 20 % by weight solution of the precursor, preferred are solution od 2-5 wt.-%. Higher or lower weight-% solutions may be used depending on solubility of the precursor in a specific solvent and specific applications. The solutions were then spin-coated or dip-coated by methods known per se in the art onto substrates, for example, silicon substrates, glass substrates, indium tin oxide substrates, and aluminum tin oxide substrates.

Thermal decomposition was carried out in a furnace under nitrogen in a temperature range of 100° C. to 10000° C., preferably 400° C. to 7000° C. Some precursor materials did not require an inert gas atmosphere and were decomposed in air, for example, Zn, Cd, Ga, In compounds. Decomposition (reaction) temperatures depend on the type of precursor and cannot be generalized. The substrate with the applied coating was introduced into the furnace heated to the desired temperature. The volatile byproducts were flushed out with the nitrogen stream. The residence times were varied from 1–30 min.

The residence time should be varied according to the thickness of the applied coating, i.e., thicker layers require a longer period of heating to complete sulfide film formation and crystallization. It has been found that a residence time of 15 min. is advantageous for many precursors.

In order to achieve the desired sulfide film thickness, it may be necessary to apply a plurality of coatings and carry out an intermediate heating step after each coating for reacting the precursor to the desired metal sulfide. Of course, the thickness of the resulting metal sulfide film layer is also determined by the concentration of the solution. A higher concentration will form a thicker metal sulfide film.

Inert gases other than nitrogen can be used during heating. Sulfide Films from Ca(SAc)$_2$·15-crown-5, Sr(SAc)$_2$·15-crown-5 and Ba(SAc)$_2$·18-crown-6

The precursors Ca(SAc)$_2$·15-crown-5, Sr(SAc)$_2$·15-crown-5 and Ba(SAc)$_2$·18-crown-6 were dissolved in ethanol to give a 5% by weight solution of the precursor. The substrates coated with the precursor solution were introduced into the furnace heated to various temperatures between 400°–700° C. for 15 min.–30 min. Care must be taken that oxygen is excluded because traces of oxygen can result in the formation of sulfates for these precursors. Satisfactory sulfide films resulted after 15 min. residence time.

It was found that temperatures lower than 400° C. for these precursors lead to undesirable amorphous films. The preferred temperature range was found to be around 700° C.

Figure 15:
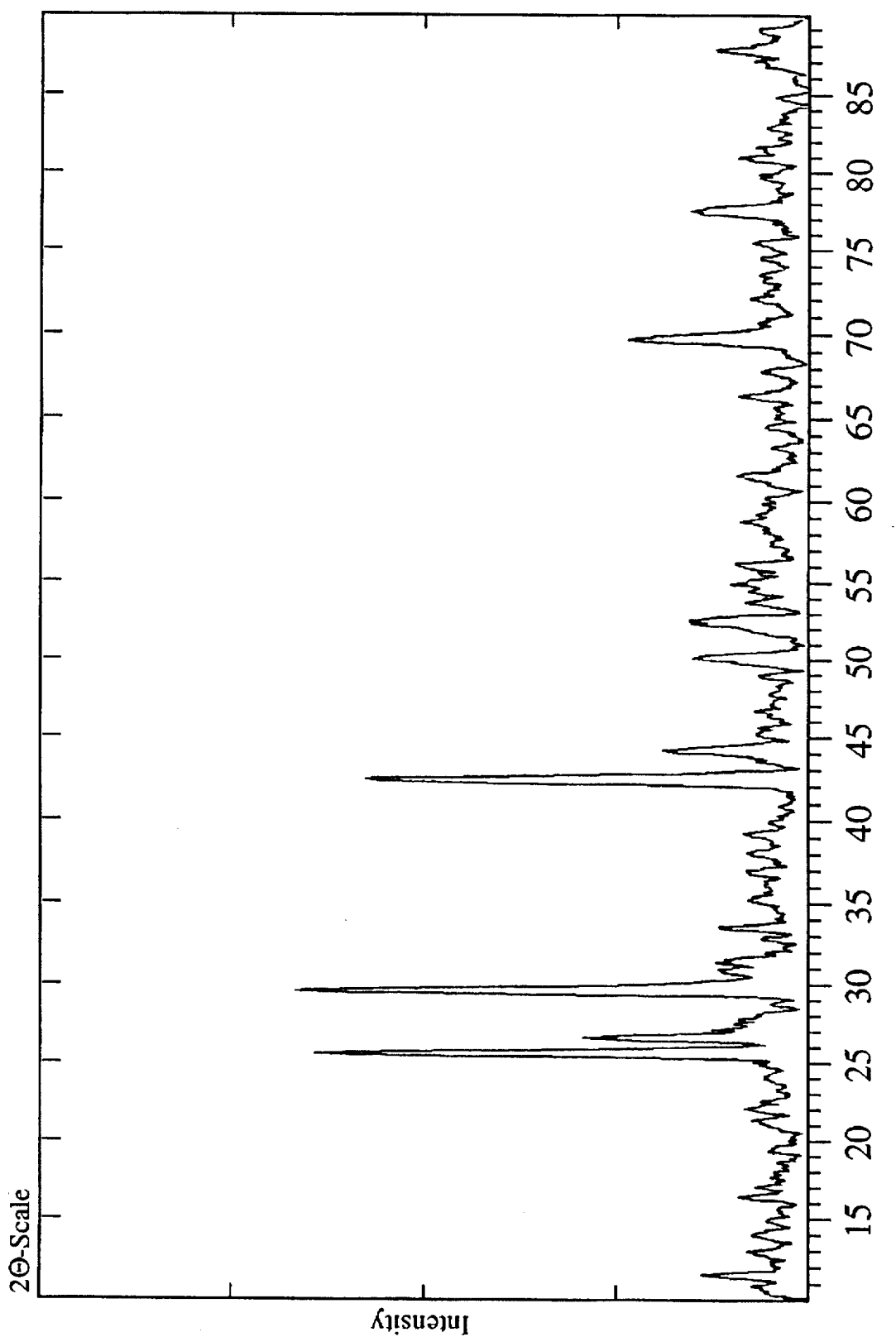
FIG. 15 shows the powder X-ray diffraction spectrum of the SrS film produced by spin-coating a solution of $Sr(SAc)_2 \cdot$ 15-crown-5 in ethanol.

The resulting CaS, SrS and BaS films were examined by X-ray powder diffraction analysis. The number and location of peaks confirmed that the produced films indeed were comprised of the respective sulfides. FIG. 15 shows as a specific example a powder X-ray diffraction spectrum of SrS formed by the aforementioned spin-coating experiment.

Scanning electron microscopy (SEM) revealed that the formed sulfide films after a single coating were approximately 100 nm thick.

Sulfide Film from [In(SOCMe)$_4$]$^+$[HNC$_5$H$_3$Me$_2$]$^-$

A light yellow clear solution was formed by dissolving 1.2 g of [In(SOCMe)$_4$]$^+$[HNC$_5$H$_3$Me$_2$]$^-$ in 40 mL THF (0.06M). A substrate wafer was dip-coated with the resulting solution. The substrate wafer was then heated to 300° C. for 20 mins. The film was examined by powder X-ray diffraction and the presence of In$_2$S$_3$ was confirmed.

Sulfide Film from LGa(SCOCH$_3$)$_2$Me (L=3,5-dimethyl pyridine)

A light orange clear solution was formed by dissolving 0.40 g of LGa(SCOCH$_3$)$_2$Me (L=3,5-dimethyl pyridine) in 20 mL pyridine. A substrate wafer was dip-coated with the resulting solution. The substrate wafer was then heated to 345° C. for 2 hrs. The film was examined by powder X-ray diffraction and the presence of Ga$_2$S$_3$ was confirmed.

MS (M=Cd, Zn) Thin Films from M(SOCR)$_2$TMEDA Precursors

The metal thiocarboxylates can also be used as precursors for thin films by solution routes. Zn(SOCCH$_3$)$_2$TMEDA (0.04 g, 0.12 mmol), was dissolved in 5 mL toluene, and Cd(SOCCH$_3$)$_2$TMEDA (0.45 g, 0.12 mmol) was dissolved in 5 mL toluene. The resulting solutions were coated onto a silicon substrate dropwise, and heated on a hot plate at 150° C. between coatings. The coated substrates were then annealed in air at 200° C. for 1 hr. to ensure completion of crystallization.

Instead of using solutions of individual precursors, it is also possible to use a combination of two or more precursors in order to produce mixed metal sulfide films. Preferred combinations are Ca/Ba and Ca/Sr. In these embodiments the precursors of different metals, for example, Ca(SaC)$_2$·L and Ba(SAc)$_2$·L are dissolved together in a solvent and subsequently spin-coated or dip-coated onto the substrate. The substrate is then heat-treated as described.

Another preferred mixed metal sulfide film is CaGa$_2$S$_4$ which is preferably produced by combining the precursors Ca(SAc)$_2$·L and Ga(SAc)$_3$·L.

More than two metal compound precursors can be used in accordance with the described procedures in order to form multi-metal sulfide films containing three, four or more different metals.

Annealing

The resulting films may be amorphous and may require an annealing step in order to convert such an intermediate amorphous film to the desired crystalline film. Such an annealing step is preferably carried out at temperatures at or below 700° C. and serves, on the one hand, to remove any volatile reaction products from the metal sulfide film and, on the other hand, to crystallize or complete crystallization of an intermediate metal sulfide film.

Doping

The single-metal or multi-metal sulfide films may also be doped in order to create the desired luminescent properties of the film. Preferred doping metals are, for example, Cu, Ag, Au, Eu, Dy, Ho, Er, Tb, Pr, Mn, and Ce. They can be added individually or in combination. The dopant level in the final metal sulfide film should be 10% or less, preferably 5% or less.

The present invention is, of course, in no way restricted to the specific disclosure of the specification, examples and drawings, but also encompasses any modifications within the scope of the appended claims.

What we claim is:

1. A method of depositing a metal sulfide film on a substrate, said method comprising the steps of:

dissolving in a solvent at least one metal compound precursor comprising at least one thiocarboxylate ligand SECR and at least one solubility-improving ligand L, to produce a solution, wherein:

a) E is selected from the group consisting of O and S and R is selected from the group consisting of alkyl, aryl, substituted alkyl, substituted aryl, halogenated alkyl, and halogenated aryl; and b) L is selected from the group of organic monodentate ligands, organic multidentate ligands, and R$^1$O ligands, wherein R$^1$O is selected from the group of alkyloxide and aryloxide;

coating the solution onto a substrate; and heating the substrate to a reaction temperature sufficient to decompose said at least one metal compound precursor to form a metal sulfide film of at least one metal on the substrate.

2. A method according to claim 1, wherein the metal of said at least one metal compound precursor is selected from the group consisting of Ca, Sr, Ba, Zn, Cd, Pb, Ga, In, Sb, and Bi.

3. A method according to claim 1, wherein said at least one metal compound precursor is M(SECR)$_n$L$_m$.

4. A method according to claim 1, wherein said at least one metal compound precursor is (R$^1$)$_n$M(SECR)$_m$ with R$^1$ selected from the group consisting of alkyl, aryl, substituted alkyl, and substituted aryl.

5. A method according to claim 1, further comprising the step of providing during heating an inert atmosphere for the substrate and the metal sulfide film.

6. A method according to claim 5, further including the step of selecting the reaction temperature to be between 100° C. and 1000° C.

7. A method according to claim 6, wherein the reaction temperature is between 400° C. and 700° C.

8. A method according to claim 1, further including the step of selecting the multidentate ligand from the group consisting of cyclic polyethers, acyclic polyethers, cyclic polyamines, and acyclic polyamines.

9. A method according to claim 8, wherein the acyclic polyethers include diglyme, triglyme, tetraglyme, and derivatives of diglyme, triglyme, and tetraglyme.

10. A method according to claim 8, wherein the polyamines include ethylene diamine and derivatives thereof and diethylene triamine and derivatives thereof.

11. A method according to claim 8, further including the step of selecting the cyclic polyether from the group of crown ethers.

12. A method according to claim 11, wherein the group of crown ethers includes 18-crown-6 ether and derivatives thereof and 15-crown-5 ether and derivatives thereof.

13. A method according to claim 1, further including the step of selecting the monodentate ligand from the group consisting of an ether and an amine.

14. A method according to claim 1, further comprising the step of annealing at an annealing temperature the metal sulfide film formed on the substrate.

15. A method according to claim 1, further including the steps of adding to the solution at least one dopant compound comprising a metal dopant selected from the group consisting of Cu, Ag, Au, Eu, Dy, Ho, Er, Tb, Pr, and Ce and selecting a concentration of said metal dopant to be less than 10 weight-% of the metal sulfide film.

16. A method according to claim 1, wherein said solution contains a first one of said metal compound precursors and a second one of said metal compound precursors to produce a mixed metal sulfide film, wherein said first metal compound precursor contains a different metal than said second metal compound precursor.

17. A method according to claim 16, wherein said solution contains a third one of said metal compound precursors and wherein said third metal compound precursors contains a different metal than said first and said second metal compound precursors.

18. A method according to claim 16, further including the steps of adding to the solution of said first and said second metal compound precursors at least one dopant compound comprising a metal dopant selected from the group consisting of Mn, Cu, Ag, Au, Eu, Dy, Ho, Er, Tb, Pr, and Ce and selecting a concentration of the metal dopant to be less than 10 weight-% of the mixed metal sulfide film.

19. A method according to claim 1, comprising the step of selecting the substrate from a group consisting of a silicon substrate, a glass substrate, an indium tin oxide substrate, and an aluminum tin oxide substrate.

* * * * *

UNITED STATES PATENT AND TRADEMARK OFFICE
CERTIFICATE OF CORRECTION

PATENT NO. : 5,744,198
DATED : April 28, 1998
INVENTOR(S) : Hampden-Smith et al

It is certified that error appears in the above-indentified patent and that said Letters Patent is hereby corrected as shown below:

Column 1, line 8, should read as follows:

N00014-94-1-0324 awarded by the Office of Naval Research.

Signed and Sealed this

Twenty-first Day of September, 1999

Attest:

Q. TODD DICKINSON

*Attesting Officer*     *Acting Commissioner of Patents and Trademarks*